(12) United States Patent
Glick et al.

(10) Patent No.: US 7,125,866 B1
(45) Date of Patent: *Oct. 24, 2006

(54) THERAPEUTIC APPLICATIONS OF PRO-APOPTOTIC BENZODIAZEPINES

(75) Inventors: Gary D. Glick, Ann Arbor, MI (US); Anthony W. Opipari, Jr., Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/700,101

(22) PCT Filed: Apr. 27, 2000

(86) PCT No.: PCT/US00/11599

§ 371 (c)(1),
(2), (4) Date: Nov. 8, 2000

(87) PCT Pub. No.: WO00/66106

PCT Pub. Date: Nov. 9, 2000

Related U.S. Application Data

(60) Provisional application No. 60/191,855, filed on Mar. 24, 2000, provisional application No. 60/165,511, filed on Nov. 15, 1999, provisional application No. 60/131,761, filed on Apr. 30, 1999.

(51) Int. Cl.
*A61K 31/55* (2006.01)

(52) U.S. Cl. .................................... 514/220
(58) Field of Classification Search ................ 514/220
See application file for complete search history.

(56) References Cited

U.S. PATENT DOCUMENTS

| | | | |
|---|---|---|---|
| 4,076,823 A | 2/1978 | Wade et al. | |
| 4,088,756 A * | 5/1978 | Voorhees ..................... | 514/47 |
| 4,110,337 A | 8/1978 | Szarvasi | |
| 4,495,101 A | 1/1985 | Klaubert et al. | |
| 4,751,223 A | 6/1988 | Glamkowski et al. | |
| 5,041,438 A | 8/1991 | Hsu | |
| 5,216,148 A * | 6/1993 | Klaus et al. ................. | 540/517 |
| 5,288,514 A | 2/1994 | Ellman ...................... | 427/29.6 |
| 5,324,726 A | 6/1994 | Bock et al. | |
| 5,591,227 A | 1/1997 | Dihn et al. | |
| 5,597,915 A | 1/1997 | Chambers et al. | |
| 5,599,352 A | 2/1997 | Dihn et al. | |
| 5,697,967 A | 12/1997 | Dihn et al. | |
| 5,776,946 A | 7/1998 | McGeer et al. ............. | 514/307 |
| 5,861,380 A | 1/1999 | Gyorkos et al. | |
| 6,004,942 A | 12/1999 | Firestein et al. | |
| 6,080,588 A | 6/2000 | Glick | |
| 6,277,844 B1 | 8/2001 | Spector et al. | |
| 6,319,931 B1 | 11/2001 | Kroemer et al. | |
| 6,506,744 B1 | 1/2003 | Alig | |
| 6,767,533 B1 | 7/2004 | Casellas | |
| 2001/0016583 A1* | 8/2001 | Glick et al. ................. | 514/220 |
| 2003/0044776 A1* | 3/2003 | Dykens et al. ................. | 435/6 |
| 2006/0025388 A1* | 2/2006 | Glick ......................... | 514/167 |

FOREIGN PATENT DOCUMENTS

| | | |
|---|---|---|
| DE | 1810423 | 10/1969 |
| EP | 0 227 539 B1 | 12/1986 |
| EP | 0 349 949 A2 | 1/1990 |
| WO | WO 90/13332 | 11/1990 |
| WO | WO 91/12779 | 9/1991 |
| WO | WO 99/29347 | 6/1999 |
| WO | WO 99/58117 | 11/1999 |
| WO | WO 00/19200 | 6/2000 |

OTHER PUBLICATIONS

Gupta et al., Psychitripic drugs in drmatology . . . , Database:EMbase(AN:86111413), Journal of the American Academy of Dermatology, 1986, vol. 14, No. 4, pp. 633-645.*
Snyder, Jane R., Chemistry & Biol., 12, (2005), 477-484.
Williams, Darren, Chemistry & Biol., 11, (2004), 1251-1259.
Parks, Daniel J. Bioorg Med Chem. Ltrs,. 15,(2005), 765-770.
Raboisson, P. Bioorg Med Chem. Ltrs., 15,(2005), 1857-1861.
Hulme, C. J. Org. Chem., 63,(1998), 8021-8023.
Kamal, A. Synlett, 14,(2004), 2533-35.
Grasberger, Bruce L., J. Med. Chem., 48, (2005), 909-912.
Beurdeley-Thomas et al., Journal of Neuro-Oncology 46 (2000) 45-56.
Churcher et al., Bioorganic & Medicinal Chemistry Letters 13 (2003) 179-183.
Darrow et al., Bioorganic & Medicinal Chemistry Letters 8 (1998) 3127-3132.

(Continued)

Primary Examiner—Vickie Kim
(74) Attorney, Agent, or Firm—Medlen & Carroll, LLP

(57) ABSTRACT

Benzodiazepinc compounds, and methods for using those compounds are provided. Some of the benzodiazepine compounds include 1,4-benzodiazepine-2-one and 1,4-benzodiazepine-2,5-dione compounds of structures (I) or (II): wherein $R_1$, $R_2$, $R_3$ and $R_4$ are as defined. The invention also includes enantiomers, pharmaceutically acceptable salts, prodrugs or derivatives of the benzodiazepine compounds. Any one or more of these benzodiazepine compounds can be used to treat a variety of dysregulatory disorders related to cellular death. Such disorders include autoimmune disorders, inflammatory conditions, hyperproliferative conditions, viral infections, and atherosclerosis. In addition, the above compounds can be used to prepare medicaments to treat the above-described dysregulatory disorders. The benzodiazepines can also be used in drugs screening assays and other diagnostic methods.

4 Claims, 15 Drawing Sheets

OTHER PUBLICATIONS

Herranz, Medicinal Research Reviews 23 (2003) 559-603.

Ramdas et al., Archieves of Biochemistry and Biophysics 368 (1999) 394-400.

Ursini et al., J. Med. Chem. 43 (2000) 3596-3613.

Walser et al., J. Org. Chem. 38:3502-3507 (1973).

Kim et al., J. Braz. Chem. Soc. 9:375-379 (1998).

Schlumpf, M., et al., "Delayed Developmental Immunotoxicity of Prenatal Benzodiazepines," Toxic. In Vitro—8(5):1061-1065(1994).

Blum P., et al., "Stiff-Person Syndrome: An Autoimmune Disease" *Movement Disorders*, 6 (1): 12-20 (1991).

Malgrange B., et al., "Beta-Carbolines Induce Apoptotic Death of Cerebellar Granule Neurones in Culture" *Neuroreport*, 7 (18): 3041-3045 (1996).

Miller, K.A., et al., "Benzodiazepines Prevent Neuronal Death By Apoptosis & Necrosis in the Gerbil Hippocampus Following Transient Cerebral Ischemia" *Society for Neuroscience Abstracts*, 24 (1-2): 979 (1998).

Schlumpf M., et al., "Delayed Developmental Immunotoxicity of Prenatal Benzodiazepines" *Toxic in Vitro*, 8 (5): 1061-1065 (1994).

Tanimoto Y., et al., "Benzodiazepine Receptor Agonists Modulate Thymocyte Apoptosis Through Reduction of the Mitochondrial Transmembrane Potential" *Jpn. J. Pharmacol.*, 79: 177-183 (1999).

Taupin V., et al., "Endogenous Anxiogenic Peptide, ODN-Diazepam-Binding Inhibitor, and Benzodiazepines Enhance the Production of Interleukin-1 and Tumor Necrosis Factor by Human Monocytes" *Lymphokine and Cytokine Research*, 10 (1): 7-13 (1991).

Blum, P., et al., "Stiff-Person Syndrome: An Autoimmune Disease," *Movement Disorders*—6(1):12-20 (1991).

Malgrange, B., et al., "β-Carbolines Induce Apoptotic Death of Cerebellar Granule Neurones in Cultures," *NeuroReport*—7(18):3041-3045 (1996).

Miller, K.A., et al., "Benzodiazepines Prevent Neuronal Death by Apoptosis & Necrosis in the Gerbil Hippocampus Following Transient Cerebral Ischemia," *Society for Neuroscience Abstracts*—24(1-2):979 (1998).

Schlumpf, M., et al., "Delayed Developmental Immunotoxicity of Prenatal Benzodiazepines," *Toxic. In Vitro*—3(5):1061-1065 (1994).

Tanimoto, Y., et al., "Benzodiazepine Receptor Agonists Modulate Thymocyte Apoptosis Through Reduction of the Mitochondrial Transmembrane Potential," *Jpn. J. Pharmacol.*—79:177-183 (1999).

Taupin, V., et al., "Endogenous Anxiogenic peptide, ODN-Diazepam-Binding Inhibitor, and Benzodiazepines Enhance the Production of Interleukin-1 and Tumor Necrosis Factor by Human Monocytes," *Lymphokine and Cytokine Research*—10(1):7-13 (1991).

Adachi, M., et al., "Aberrant Transcription Caused by the Insertion of an Early Transposable Element in an Intron of the Fas Antigen Gene of *lpr* Mice," *Proc. Natl. Acad. Sci. USA*—90:1756-1760 (1993).

Adelman, N.E., et al., "Treatment of (NZB X NZW)$F_1$ Disease with Anti-I-A Monoclonal Antibodies," *J. Exp. Med.*—158:1350-1355 (1983).

Baader, S.L., et al., "Uptake and Cytotoxicity of Ascorbic Acid and Dehydroascorbic Acid in Neuroblastoma (SK-N-SH) and Neuroectodermal (SK-N-LO) Cells," *Anticancer Research*—14:221-228 (1994).

Beale, P.J., et al., "BCL-2 Family Protein Expression and Platinum Drug Resistance in Ovarian Carcinoma," *British Journal of Cancer*—82(2):436-440 (2000).

Boojamra, C.G., et al., "Solid-Phase Synthesis of 1,4-Benzodiazepine-2,5-Diones. Library Preparation and Demonstration of Synthesis Generality," *J. Org. Chem.*—62:1240-1256 (1997).

Bunin, B.A., et al., "A General and Expedient Method for the Solid-Phase Synthesis of 1,4-Benzodiazepine Derivatives," *J. Am. Chem. Soc.*—114:10997-10998 (1992).

Bunin, B.A., et al., "The Combinatorial Synthesis and Chemical and Biological Evaluation of a 1,4-Benzodiazepine Library," *Proc. Natl. Acad. Sci. USA*—91:7408-4712 (1994).

Chumakov, A.M., et al., "Analysis of p53 Transactivation Through High-Affinity Binding Sites," *Oncogene*—8:3005-3011 (1993).

Cohen, P.L., et al., "*Lpr* and *gld*: Single Gene Models of Systemic Autoimmunity and Lymphoproliferative Disease," *Annu. Rev. Immunol.*—9:243-269 (1991).

Crabtree, R.H., "A New Type of Hydrogen Bond," *Science*—282:2000-2001 (1998).

Desoize, B., "Anticancer Drug Resistance and Inhibition of Apoptosis," *Anicancer Research*—14:2291-2294 (1994).

Doble, A., et al., "Labelling of Peripheral-Type Benzodiazepine Binding Sites in Human Brain with [$^3$H]PK 11195: Anatomical and Subcellular Distribution," *Brain Research Bulltetin*—18:49-61 (1987).

Donadio, J.V., et al., "Immunosuppressive Drug Therapy in Lupus Nephritis," *American Journal of Kidney Diseases*—21(3):239-250 (1993).

Ermak, T.H., et al., "Treatment of Murine Lupus with Monoclonal Antibody to L3T4," *Laboratory Investigation*—61(4):447-456 (1989).

Gallant, J.E., et al.,"Incidence and Natural History of Cytomegalovirus Disease in Patients with Advanced Human Immunodeficiency Virus Disease Treated with Zidovudine," *The Journal of Infectious Diseases*—166:1223-1227 (1992).

Garcia-Calvo, M., et al. "Inhibition of Human Caspases by Peptide-Based and Macromolecular Inhibitors," *The Journal of Biological Chemistry*—273(49):32608-32613 (1998).

Gorczyca, W., et al., "Induction of DNA Strand Breaks Associated with Apoptosis During Treatment of Leukemias," *Leukemia*—7(5):659-670 (1993).

Gordon, C., et al.. "Chronic Therapy with Recombinant Tumor Necrosis Factor-α in Autoimmune NZB/NZW $F_1$ Mice," *Clinical Immunology and Immunopathology*—52:421-434 (1989).

Gordon, E.M., et al., "Applications of Combinatorial Technologies to Drug Discovery. 2. Combinatorial Organic Synthesis, Library Screening Strategies, and Future Directions," *Journal of Medicinal Chemistry*—37(10):1385-1401 (1994).

Hahn, B.H., et al., "Influence of Cyclophosphamide and Other Immunosuppressive Drugs on Immune Disorders and Neoplasia in NZB/NZW Mice," *Arthritis and Rheumatism*—18(2):145-152 (1975).

Hang, L., et al., "A Spontaneous Rheumatoid Arthritis-Like Disease in MRL/1 Mice," *J. Exp. Med.*—155:1690-1701 (1982).

Horowitz, R.E., et al., "Cyclophosphamide Treatment of Mouse Systemic Lupus Erythematosus," *Laboratory Investigation*—21(3):199-206 (1969).

Itoh, N., et al., "The Polypeptide Encoded by the cDNA for Human Cell Surface Antigen Fas Can Mediate Apoptosis," *Cell*—66:233-242 (1991).

Koopman, W.J., et al., "The MRL-lpr/lpr Mouse. A Model for the Study of Rheumatoid Arthritis," *Scand. J. Rheumatology—Suppl* 75:284-289 (1988).

Korsmeyer, S.J., "Bcl-2 Initiates a New Category of Oncogenes: Regulators of Cell Death," *Blood*—80(4):879-886 (1992).

Liu, J.R., et al., "Bcl-$x_L$ is Expressed in Ovarian Carcinoma and Modulates Chemotherapy-Induced Apoptosis," *Gynecologic Oncology*—70:398-403 (1998).

Los, M., et al., "The Role of Caspases in Development, Immunity, and Apoptotic Signal Transduction: Lessons from Knockout Mice," *Immunity*—10:629-639 (1999).

Luria, et al., *General Viology*—3$^{rd}$ edition, pp. 436-446 (1978)—Eds. John Wiley & Sons, New York.

Marino, M., et al., "Prevention of Systemic Lupus Erythematosus in MRL/*lpr* Mice by Administration of an Immunoglobulin-Binding peptide," *Nature Biotechnology*—18:735-739 (2000).

McDonnell, T.J., et al., "Progression from Lymphoid Hyperplasia to High-Grade Malignant Lymphoma in Mice Transgenic for the t(14;18)," *Nature*—349:254-256 (1991).

Nagata, S., "Human Autoimmune Lymphoproliferative Syndrome, a Defect in the Apoptosis-Inducing Fas Receptor: A Lesson from the Mouse Model," *J. Hum. Genet.*—43:2-8 (1998).

Okuyama, H., et al., "Analysis of Defective Delayed-Type Hypersensitivity in Autoimmune Mice Bearing *lpr* Gene," *Clin. Exp. Immunol.*—63:87-94 (1986).

Okuyama, H., et al., "Effect of Cyclophosphamide Pretreatment on Defective Delayed-Type Hypersensitivity in Autoimmune-Prone MRL Mice," *Int. Arch. Allergy Appl. Immunol.*—88:394-401 (1989).

Ozols, R.F., "Paclitaxel Plus Carboplatin in the Treatment of Ovarian Cancer," *Seminars in Oncology*—26(1)(Supp. 2):84-89 (1999).

Pestell, K.E., et al., "Characterisation of the *P53* Status, BCL-2 Expression and Radiation and Platinum Drug Sensitivity of a Panel of Human Ovarian Cancer Cell Lines," *Int. J. Cancer*—77:913-918 (1998).

Raynaud, F.I., et al., "Intracellular Metabolism of the Orally Active Platinum Drug JM216: Influence of Glutathione Levels," *Br. J. Cancer*—74(3):380-386 (1996).

Russell, J.H., et al., "Mature T Cells of Autoimmune *lpr/lpr* Mice have a Defect in Antigen-Stimulated Suicide," *Proc. Natl. Acad. Sci. USA*—90:4409-4413 (1993).

Sakata, K., et al., "Role of Fas/FasL Interaction in Physiology and Pathology: The Good and the Bad," *Clinical Immunology and Immunopathology*—87(1):1-7 (1998).

Sandstrom, P.A., et al., "Autocrine Production of Extracellular Catalase Prevents Apoptosis of the Human CEM T-Cell Line in Serum-Free Medium," *Proc. Natl. Acad. Sci. USA*—90:4708-4712 (1993).

Schoemaker, H., et al., "Specific High-Affinity Binding Sites for [$^3$H]Ro5-4864 in Rat Brain and Kidney," *The Journal of Pharmacology and Experimental Therapeutics*—225(1):61-69 (1983).

Schwab, M., et al., "Amplified DNA with Limited Homology to *myc* Cellular Oncogene is Shared by Human Neuroblastoma Cell Lines and Neuroblastoma Tumour," *Nature*—305:245-248 (1983).

Scott, C.F., et al., "Comparison of Antigen-Specific T Cell Responses in Autoimmune MRL/mp-lpr/lpr and MRL/Mp-+/+ Mice," *The Journal of Immunology*—132(2):633-639 (1984).

Sentman, C.L., et al., "bcl-2 Inhibits Multiple Forms of Apoptosis but not Negative Selection in Thymocytes," *Cell*—67:879-888 (1991).

Sheppard, R.C., et al., "Acid-Labile Resin Linkage Agents for Use in Solid Phase Peptide Synthesis," *Int. J. Peptide Protein Res.*—20:451-454 (1982).

Stevens, S.Y., et al., "Non Nucleic Acid Inhibitors of Protein-DNA Interactions Identified Through Combinatorial Chemistry," *J. Am. Chem. Soc.*—118:10650-10651 (1996).

Sugimoto, T., et al., "Determination of Cell Surface Membrane Antigens Common to Both Human Neuroblastoma and Leukemia-Lymphoma Cell Lines by a Panel of 38 Monoclonal Antibodies," *JNCI*—73(1):51-57 (1984).

Swanson, P.C., et al., "High Resolution Epitope Mapping of an Anti-DNA Autoantibody Using Model DNA Ligands," *J. Immunology*—152(5):2601-2612 (1994).

Swanson, P.C., et al., "Ligand Recognition by Murine Anti-DNA Autoantibodies," *J. Clin. Invest.*—97(7):1748-1760 (1996).

Takahashi, T., et al., "Generalized Lymphoproliferative Disease in Mice, Caused by a Point Mutation in the Fas Ligand," *Cell*—76:969-976 (1994).

Theofilopoulous, A.N., et al., "Murine Models of Systemic Lupus Erythematosus," *Advances in Immunology*—37:269-390 (1985).

Thompson, C.B., "Apoptosis in the Pathogenesis and Treatment of Disease," *Science*—267:1456-1462 (1995).

Watanabe-Fukunaga, R., et al., "Lymphoproliferation Disorder in Mice Explained by Defects in Fas Antigen that Mediates Apoptosis," *Nature*—356:314-317 (1992).

White, E., "Life, Death, and the Pursuit of Apoptosis," *Genes & Development*—10:1-15 (1996).

Wu, G.Y., et al., "Receptor-Mediated *In Vitro* Gené Transformation by a Soluble DNA Carrier System," *The Journal of Biological Chemistry*—262(10):4429-4432 (1987).

Wyllie, A.H., "The Genetic Regulation of Apoptosis," *Current Opinion in Genetics & Development*—5:97-104 (1995).

Zamzami, N., et al., "Mitochondrial Control of Nuclear Apoptosis," *J. Exp. Med.*—183:1533-1544 (1996).

Zoratti, M., et al., "The Mitochondrial Permeability Transition," *Biochimica et Biophysica Acta*—1241:139-176 (1995).

Dichek, D.A., "Seeding of Intravascular Stents With Genetically Engineered Endothelial Cells" Laboratory Investigation, vol. 80, No. 5, pp. 1347-1353, Nov. 1989.

Don, A.S., et al., "A peptide trivalent arsenical inhibits tumor angiogenesis by perturbing mitochondrial function in angiogenic endothelial cells" Cancer Cell, vol. 3, pp. 497-509, May 2003.

Atwal, K.S., et al., "Small Molecule Mitochondrial F1F0 ATPase Hydrolase Inhibitors as Cardioprotective Agents", J. Med. Chem. 47, pp. 1081-1084(2004).

Hamann, L.G., et al., "Benzodiazepine-based slective inhibitors of mitochondrial F1F0 ATP hydrolase", Bioorganic & Medicinal Chemistry Ltrs., vol. 14, pp. 1031-1034 (2004).

* cited by examiner (a) [4-(hydroxymethyl)phenoxy] acetic acid with polystyrene support;
(b) 20% piperidine in DMF;
(c) N-FMOC-amino acid fluoride, 4-methyl-2, 6-di-tert-butylpyridine;
(d) 5% acetic acid in DMF, 60 °C;
(e) lithiated 5-(phenylmethyl)-2-oxazolidinone in THF, 78 °C, followed by alkylating agents in DMF;
(f) TFA/H$_2$O/Me$_2$S (85:5:10)

Compound 1

Bz kills D2 neuroblastoma cells in vitro. D2 neuroblastoma cells were treated with increasing concentrations of Bz in culture media containing 1% FBS and 1% DMSO. After 18 hours, viability was assessed with the MTT assay and expressed as percent of DMSO control.

2B1 and SKOV3 cells are resistant to CDDP. Ovarian Cancer cell lines were treated in culture media containing 2% FBS with increasing concentrations of CDDP. Cell death was measured after 24 hours of treatment by flow cytometry on the basis of propidium iodide uptake. Data presented as mean value with standard deviation.

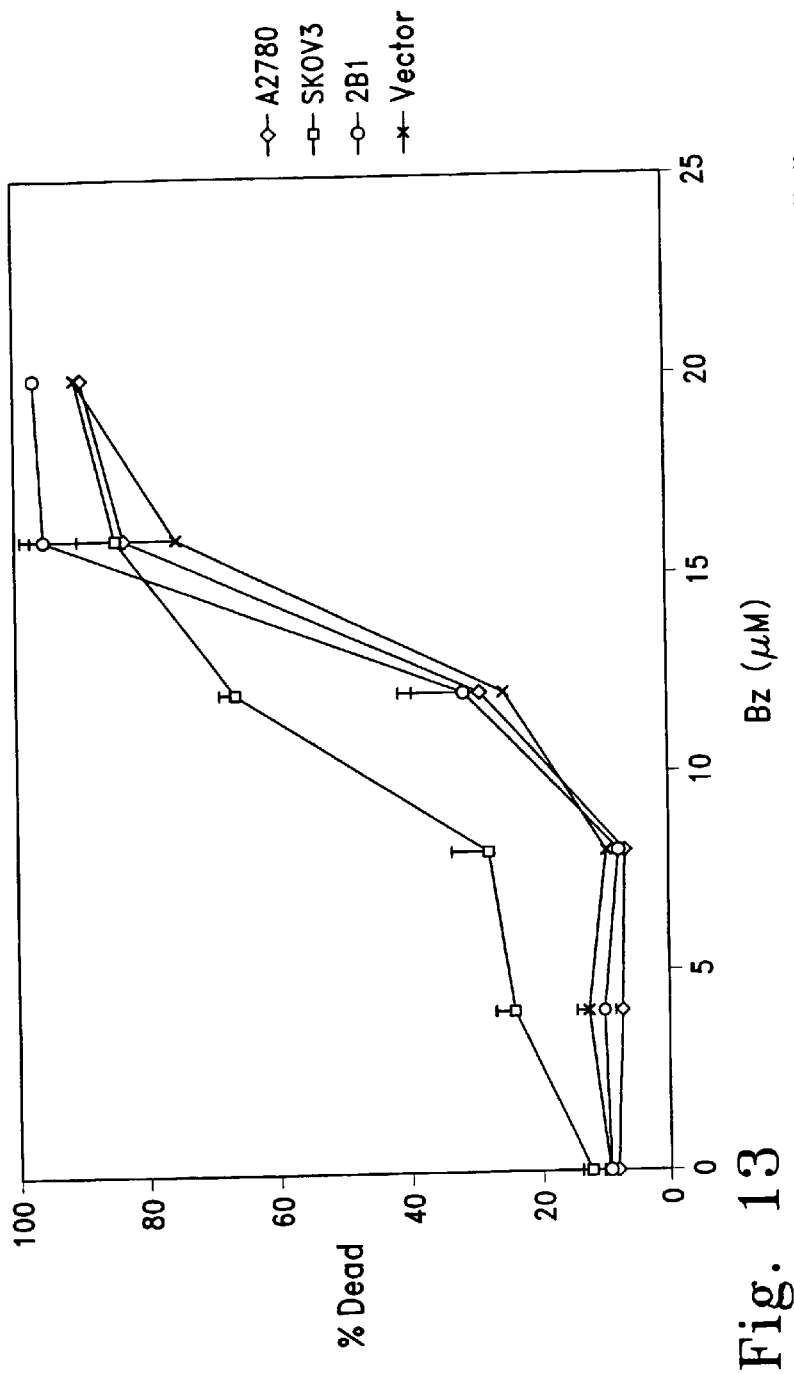
Fig. 13  Ovarian cancer cells are killed by Bz. Ovarian cancer cell lines were treated in culture media containing 2% FBS and 1% DMSO with increasing concentrations of Bz. Cell death was measured after 24 hous of treatment by flow cytometry on the basis of propidium iodide uptake. Data presented as mean value with standard deviation.

THERAPEUTIC APPLICATIONS OF PRO-APOPTOTIC BENZODIAZEPINES

CROSS-REFERENCE TO RELATED APPLICATIONS

The present disclosure claims priority to U.S. Provisional Application Nos. 60/191,855, filed Mar. 24, 2000; 60/131,761, filed Apr. 30, 1999; and 60/165,511, filed Nov. 15, 1999, the contents of which are hereby incorporated by reference.

FIELD OF THE INVENTION

The present invention is in the field of medicinal chemistry and relates to other areas such as pharmacology, biochemistry and organic chemistry. In particular, it provides novel chemical compounds, and their therapeutic uses.

BACKGROUND

Multicellular organisms exert precise control over cell number. The normal structure and function of tissues depends on the maintenance of appropriate cell numbers. A balance between cell proliferation and cell death (White, E. (1996) *Genes Dev.* 10:1–15) achieves this homeostasis.

Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism (Wyllie, A. H. (1995) *Curr. Opin. Gen. Dev.* 5:97–104). As a regulatory process, apoptosis influences diverse biological phenomena including the development of neural architecture, the immune system's ability to discriminate between self and non-self, and the expunging of redundant, damaged or infected cells.

It has become evident that many diseases are associated with dysregulation of the process of cell death. Experimental models have established a cause-effect relationship between derangement in the mechanism regulating apoptosis or necrosis and the pathenogenicity of various neoplastic, autoimmune and viral diseases (Thompson, C. B. (1995) *Science* 267:1456–1462). A well-defined example is the effect of aberrant, high-level expression of bcl-2 on lymphoma development. The bcl-2 oncogene was originally identified as the genetic element located at the t(14:18) chromosomal translocation breakpoint present in many B-cell follicular lymphomas (Korsmeyer, S. J. (1992) *Blood* 359:554–556). Since that discovery, it has been convincingly established that the bcl-2 gene product inhibits apoptosis induced by a variety of stimuli and that its oncogenic potential stems from its ability to derail apoptosis (Sentman, C. L. et al. (1994) *Cell* 67:878–888; and McDonnell, T. J. and Korsmeyer, S. J. (1991) *Nature* 349:254–256).

Failed or reduced apoptosis is associated with the development of human autoimmune lymphoproliferative syndrome as well as mouse models of this disease. MRL-lpr or gld mice develop lymphadenopathy, splenomegaly, nephritis and arthritis; as well they produce large quantities of autoantibodies (Cohen, P. L. and Eisenberg, R. A. (1991) *Annu. Rev. Immunol.* 9:243–269).

These mice carry loss of function mutations in the genes encoding FAS and Fas ligand, respectively (Adachi, M. et al. (1993) *Proc. Natl. Acad. Sci. USA* 90:1756–1760); Takakashi, T. et al. (1994) *Cell* 76:969–976). FAS, a ubiquitously expressed cell surface receptor, normally generates an apoptotic response upon binding with Fas ligand (Itoh, N. et al. (1991) *Cell* 66:233–243). In mice carrying these loss of function mutations, the disruption of FAS signaling renders T cells resistant to peripheral deletion by apoptosis (Russell, H. et al. *Proc. Natl. Acad. Sci. USA* 90:4409–4413). The inappropriate survival of these cells results in a pathologic accumulation of T and B cells evidenced by the neoplastic-like growth of lymphoid tissues and high-level autoantibody production. In humans, autoimmune lymphoproliferative syndrome shares similarities with the mouse phenotype including lymphadenopathy, splenomegaly, autoantibodies and autoimmune manifestations. Patients with this disease likewise carry mutation in the FAS gene (Nagata, S. (1998) *J. Hum. Genet.* 43:2–8).

Benzodiazepine compounds have been traditionally known to bind to benzodiazepine receptors in the central nervous system (CNS) and thus have been used to treat various CNS disorders including anxiety and epilepsy. More recently, peripheral benzodiazepine receptors have also been identified, which receptors may incidentally also be present in the CNS. Benzodiazepines and related structures have pro-apoptotic and cytotoxic properties useful in the treatment of transformed cells grown in tissue culture. There is therapeutic potential for this class of agents against cancer and other neoplastic diseases. Two specific examples shown are neuroblastoma and ovarian cancer.

Neuroblastoma is the most common extracranial solid tumor found in children. Modern treatments, which include chemotherapy, radiation therapy and surgery, have not significantly reduced the mortality of metastatic neuroblastoma. Novel therapies are needed to improve survival of children with this disease. We show that benzodiazepine compounds are able to slow the growth of these tumor cells. See, Sugimoto, T. et al. (1984) *J. Natl. Cancer Inst.* 73:51–57; Schwab, M. et al. (Sep. 15, 1983) *Nature* 305:245–248; and Dive, C. and Wyllie, A. H. (1993) *Apoptosis and Cancer Chemotherapy*, Oxford Blackwell, pp. 21–56.

Ovarian cancer is difficult to treat due to chemoresistance shown by the patient to standard chemotherapy drugs. Treatment failures are usually attributed to the emergence of chemotherapy resistant cells. We show that benzdiazepine compounds are able to kill ovarian cancer cells that are chemoresistant. See, Pestell, K. E. et al. (1998)*Int. J. Cancer* 77(6):913–918; Beale, P. J. et al. (2000) *Br. J. Cancer* 82(2):436–440; Ozols, R. F. (February 1999) *Semin. Oncol.* 26(1 Suppl. 2):84–89; Liu, J. R. et al. (September 1998) *Gynecol. Oncol.* 70(3):398–403; Chumakov, A. M. et al. (November 1993) *Oncogene* 8(11):3005–3011; and Raynaud, F. I. et al. (August 1996) *Br. J. Cancer* 74(3):380–386.

Several benzodiazepine analogs have been reported as analgesic and anti-inflammatory agents. See, for example, U.S. Pat. Nos. 4,076,823, 4,110,337, 4,495,101, 4,751,223 and 5,776,946.

U.S. Pat. Nos. 5,324,726 and 5,597,915 disclose that some benzodiazepines are antagonists of cholecystokinin and gastrin and thus might be useful to treat certain gastrointestinal disorders.

Certain benzodiazepines have also been explored as inhibitors of human neutrophil elastase and thus potentially useful to treat the human neutrophil elastase-mediated conditions such as myocardial ischemia, septic shock syndrome, among others. See U.S. Pat. No. 5,861,380.

U.S. Pat. No. 5,041,438 reported that certain benzodiazepines could be useful as anti-retroviral agents. However, as it will become apparent from the description below, the present invention provides novel methods and compositions that are distinct from the above-disclosed methods and compositions.

DISCLOSURE OF THE INVENTION

This invention provides methods for treating a condition associated with dysregulation of the process of cell death in a subject, comprising administering to the subject an effective amount of a benzodiazepine compound. In one aspect, the benzodiazepines of the class are identified by their inability to bind to a central benzodiazepine receptor or with low affinity to a peripheral benzodiazepine receptor. In a further aspect, the benzodiazepines of the class are identified by having the ability to induce cell death under condition of low serum as defined, infra. In a further aspect, the class of benzodiazepines are identified by having both of these above-noted characteristics. In a yet further aspect of this invention, chronic inflammatory conditions are specifically excluded from the group of conditions that can be treated by any class or specific compounds of the class of benzodiazepines identified herein.

In one aspect, the benzodiazepine compounds have the structure:

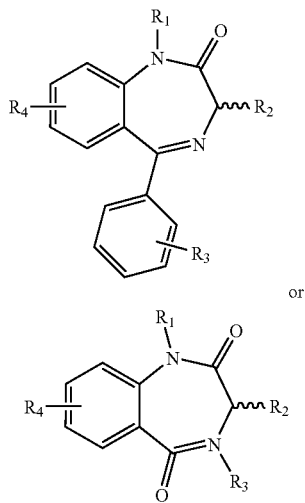

or

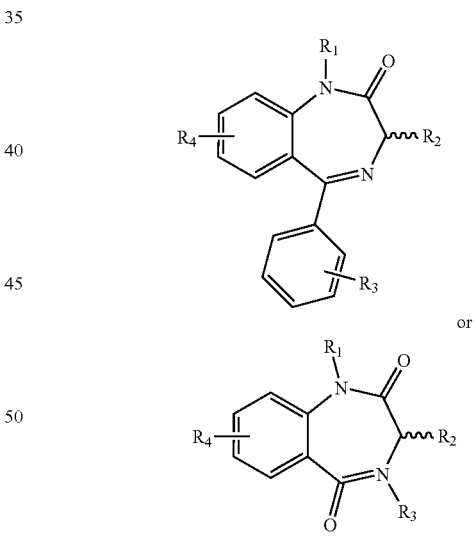

or its enantiomer, wherein, $R_1$ is aliphatic or aryl;

$R_2$ is aliphatic, aryl, —$NH_2$, —NHC(=O)—$R_5$, or a moiety that participates in hydrogen bond formation, wherein $R_5$ is aryl, heterocyclic, —$R_6$—NH—C(=O)—$R_7$ or —$R_6$—C(=O)—NH—$R_7$, wherein $R_6$ is an aliphatic linker of 1–6 carbons and $R_7$ is aliphatic, aryl, or heterocyclic; and each of $R_3$ and $R_4$ is independently hydrogen, hydroxy, alkoxy, halo, amino, lower-alkyl-substituted-amino, acylamino, hydroxyamino, an aliphatic group having 1–8 carbons and 1–20 hydrogens, aryl, or heteroaryl;

or a pharmaceutically acceptable salt, prodrug or derivative thereof.

The cell death can be induced by necrosis, apoptosis or regulation of the FAS pathway. The conditions associated with the dysregulation of a process of cell death include but are not limited to: autoimmune diseases such as systemic lupus erythematosus, rheumatoid arthritis, Sjögren's syndrome, graft-versus-host-disease, and myasthenia gravis; chronic inflammatory conditions such as psoriasis, asthma, and Crohn's disease; hyperproliferative disorders or neoplasms such as a B-cell or a T-cell lymphomas; and other conditions such as osteoarthritis and atherosclerosis. Methods are also provided for using the benzodiazepine compounds to treat the conditions associated with the dysregulation of cell death, wherein the condition is induced by a viral infection. In addition, in some aspects, methods are provided to treat a viral infection by using the benzodiazepines of the present invention.

Methods are also provided to co-administer one or more additional agents with the benzodiazepines of the present invention, wherein such additional agents may include antineoplastic agents, immunosuppressants, anti-inflammatory agents, antiviral agents, or radiation.

The cell death to be achieved by the methods and compositions of this invention involve the cell or cells present in a tissue that are: autoimmunogenic or affected by an autoimmune disorder; inflammatory or affected by inflammation; hyperproliferative; viral-infected; atherosclerosed or osteoarthritic.

Assay and diagnostic methods are also provided to identify agents useful to treat a condition associated with dysregulation of the process of cell death in a subject wherein the ability of a potential candidate agent to induce cell death is assayed by contacting the dysregulated cell with a benzodiazepine compound. The assay includes maintaining the suitable cell or tissue preferably in a low serum.

Methods are also presented to prepare medicaments to treat a condition associated with dysregulation of the process of cell death in a subject, wherein the conditions, the affected cells or tissue and the benzodiazepine compounds are described as above. The invention also provides novel 1,4-benzodiazepine compounds having the structure:

or its enantiomer,
wherein,
$R_1$ is aliphatic or aryl;
$R_2$ is —NHC(=O)—$R_5$,
wherein $R_5$ is aryl, heterocyclic, —$R_6$—NH—C(=O)—$R_7$ or —$R_6$—C(=O)—NH—$R_7$, wherein R6 is an aliphatic linker of 1–6 carbons and $R_7$ is aliphatic, aryl, or heterocyclic; and each of $R_3$ and $R_4$ is independently hydrogen, hydroxy, alkoxy, halo, amino, lower-alkyl-substituted-amino, acylamino, hydroxyamino, an aliphatic group having 1–8 carbons and 1–20 hydrogens, aryl, or heterocyclic; or a pharmaceutically acceptable salt, prodrug or derivative thereof.

These various methods, uses, and compositions are further described in greater detail below.

BRIEF DESCRIPTION OF THE DRAWINGS

FIG. 4C is a graphical analysis.

FIG. 6A shows dose-response lymphotoxicity of Compound 1. Relative viability expresses viable cells after treatment as a percentage of viable control cells to allow meaningful comparison between multiple experiments. FIG. 6B shows a comparison of Compound 1 to other ligands of benzodiazepine receptors and protection against Compound 1 killing by CsA. Compounds were compared at 10 and 20 µM, 10 µM results shown. At 20 µM, only Compound 1 demonstrated any cytotoxic effect (data not shown).

FIG. 13 is a graph that shows that ovarian cancer cells are killed by application of benzodiazepine in vitro.

MODES FOR CARRYING OUT THE INVENTION

Figure 1:
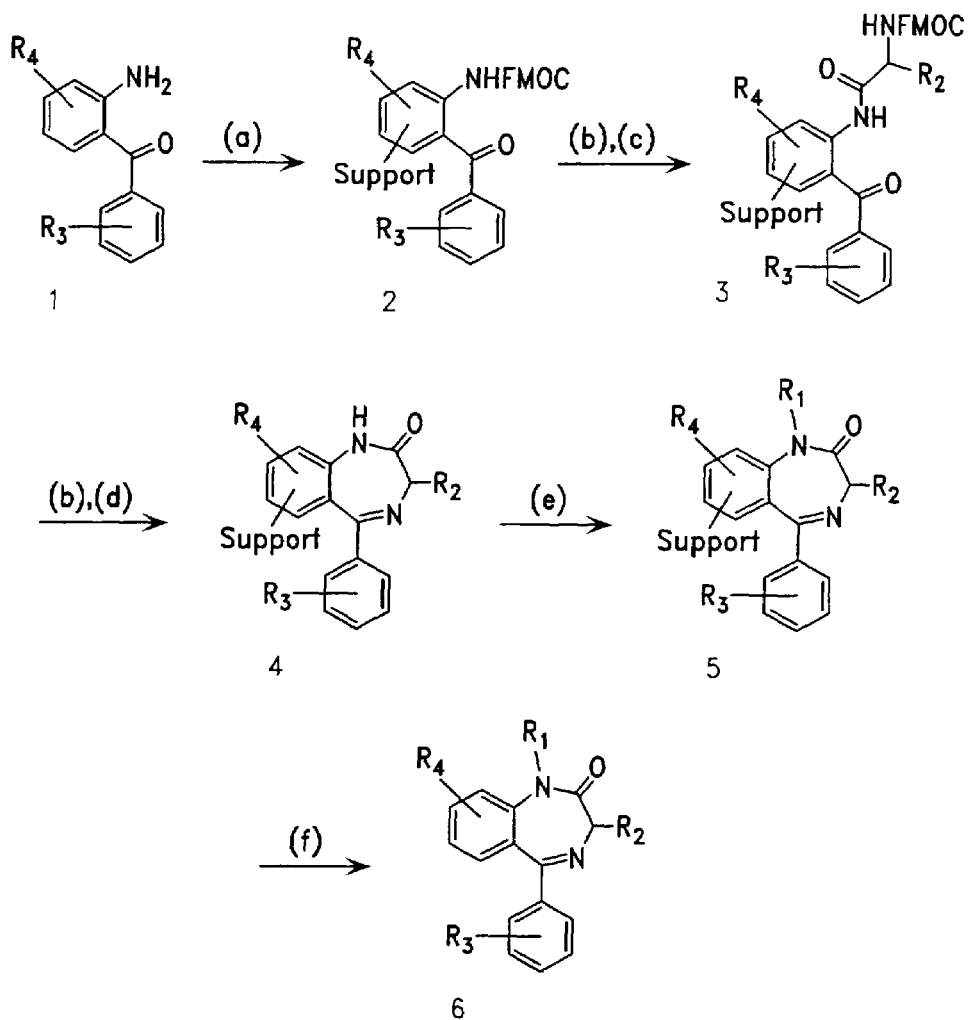
FIG. 1 shows a general synthetic scheme for solid-phase synthesis of 1,4-benzodiazepine 2-one compounds of the present invention.

Throughout this disclosure, various publications, patents and published patent specifications are referenced by an identifying citation. The disclosures of these publications, patents and published patent specifications are hereby incorporated by reference into the present disclosure to describe more fully the state of the art to which this invention pertains.

A. General Techniques

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "MOLECULAR CLONING: A LABORATORY MANUAL" Second Edition (Sambrook et al., 1989); "OLIGONUCLEOTIDE SYNTHESIS" (M. J. Gait, ed., 1984); "ANIMAL CELL CULTURE" (R. I. Freshney, ed., 1987); the series "METHODS IN ENZYMOLOGY" (Academic Press, Inc.); "HANDBOOK OF EXPERIMENTAL IMMUNOLOGY" (D. M. Weir & C. C. Blackwell, eds.); "GENE TRANSFER VECTORS FOR MAMMALIAN CELLS" (J. M. Miller & M. P. Calos, eds., 1987); "CURRENT PROTOCOLS IN MOLECULAR BIOLOGY" (F. M. Ausubel et al., eds., 1987, and periodic updates); "PCR: THE POLYMERASE CHAIN REACTION" (Mullis et al., eds., 1994); and "CURRENT PROTOCOLS IN IMMUNOLOGY" (J. E. Coligan et al., eds., 1991).

B. Definitions

As used herein, certain terms may have the following defined meanings. As used in the specification and claims, the singular form "a," "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "benzodiazepine" refers to a seven membered non-aromatic heterocyclic ring fused to a phenyl ring wherein the seven-membered ring has two nitrogen atoms, as part of the heterocyclic ring. In some aspects, the two nitrogen atoms are in 1 and 4 positions, as shown in the general structure below.

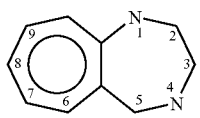

The benzodiazepine can be substituted with one keto group (typically at the 2-position), or with two keto groups (one each at the 2- and 5 positions). When the benzodiazepine has two keto groups (i.e., one each at the 2 and 5 positions), it is referred to as benzodiazepine-2,5-dione. Most generally, the benzodiazepine is further substituted either on the six-membered phenyl ring or on the seven-membered heterocyclic ring or on both rings by a variety of substituents. These substituents are described more fully below.

The term "dysregulation of the process of cell death" is intended to encompass any aberration in the ability of (or predisposition of) a cell to undergo cell death via either necrosis or apoptosis. Dysregulation of cell death is associated with or induced by a variety of conditions, including for example, autoimmune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "subject" is a vertebrate, preferably a mammal, more preferably a human. Mammals include, but are not limited to, murines, simians, humans, farm animals, sport animals, and pets.

An "effective amount" is an amount sufficient to effect beneficial or desired results. An effective amount can be administered in one or more administrations, applications or dosages.

An "autoimmune disorder" is any condition in which an organism produces antibodies or immune cells which recognize the organism's own molecules, cells or tissues. Non-limiting examples of autoimmune disorders include rheumatoid arthritis, Sjögren's syndrome, graft versus host disease, myasthenia gravis, and systemic lupus erythematosus.

A "hyperproliferative disorder" is any condition in which a localized population of proliferating cells in an animal is not governed by the usual limitation of normal growth. Examples of hyperproliferative disorders include tumors, neoplasms, lymphomas and the like. A neoplasm is said to be benign if it does not undergo, invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

A "chronic inflammatory condition" shall mean those conditions that are characterized by a persistent inflammatory response with pathologic sequelae. This state is characterized by infiltration of mononuclear cells, proliferation of fibroblasts and small blood vessels, increased connective tissue, and tissue destruction. Examples of chronic inflammatory diseases include Crohn's disease, psoriasis, and asthma. Autoimmune diseases such as rheumatoid arthritis and systemic lupus erythematosus can also result in a chronic inflammatory state.

The "co-administration" refers to administration of more than one agent or therapy to a subject. By "sensitizing agent" is meant any agent which increases the sensitivity of a target cell or tissue to other therapeutic agents. In the context of the present invention, co-administration of the claimed compounds results in a surprising and unexpected therapeutic effect, particularly in the treatment of conditions in which apoptosis or necrosis is dysregulated. The compounds described herein also appear to sensitize target cells to the therapeutic actions of other agents.

Co-administration may be concurrent or, alternatively, the chemical compounds described herein may be administered in advance of or following the administration of the other agent(s). The appropriate dosage for co-administration can be readily determined by one skilled in the art. When co-administered with another therapeutic agent, both the agents may be used at lower dosages. Thus, co-administration is especially desirable where the claimed compounds are used to lower the requisite dosage of known toxic agents. "Toxic" refers to any detrimental or harmful effects on a cell or tissue.

A "composition" is intended to mean a combination of active agent and another compound or composition, inert (for example, a solid support, a detectable agent or label) or active, such as an adjuvant.

As used herein, "solid phase support" or "solid support," used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem, Inc., Peninsula Laboratories, etc.), POLYHIPE(®) resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California).

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARMACEUTICAL SCIENCES, 15th Ed., Mack Publ. Co., Easton, Pa. (1975).

"Pharmaceutically acceptable salt, prodrug or derivative" as used herein, relate to any pharmaceutically acceptable salt, ester, ether, salt of an ester, solvate, such as ethanolate, or other derivative of a compound of the present invention which, upon administration to a recipient, is capable of providing (directly or indirectly in the case of a prodrug) a compound of this invention or an active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system).

As is known to those of skill in the art, "salts" of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl. Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases that are non-pharmaceutically acceptable may also find use, for example, in the preparation or purification of a pharmaceutically acceptable compound.

The term "derivative" of a compound as used herein, means a chemically modified compound wherein the chemical modification takes place either at a functional group of the compound or on the aromatic ring. Non-limiting examples of 1,4-benzodiazepine derivatives of the present invention may include N-acetyl, N-methyl, N-hydroxy groups at any of the available nitrogens in the compound. Additional derivatives may include those having a trifluoromethyl group on the phenyl ring.

C. Methods of Treatment

The therapeutic potential for using benzodiazepines for their pro-apoptotic and cytotoxic properties is great. The class of agents is effective in treating cancers and other neoplastic diseases. As noted above, the present invention provides methods of treating conditions that are, in one embodiment, related in that they arise as the result of dysregulation of the normal process of cell death in the cells or tissue of a subject.

For the purpose of illustration only, such conditions include, but are not limited to autoimmune disorders (e.g., systemic lupus erythematosus, rheumatoid arthritis, graft-versus-host disease, Sjögren's syndrome and myasthenia gravis); hyperproliferative disorders, (such as—B or T cell lymphoma, neuroblastoma, and chronic lymphocytic leukemia); chronic inflammatory conditions (such as psoriasis, asthma, or Crohn's disease); other conditions such as osteoarthritis and atherosclerosis; and those induced by DNA and/or RNA viral infections, wherein the viruses include but are not limited to, herpes virus, papilloma virus and human immunodeficiency virus (HIV).

These disorders are treated by administering an effective amount of the benzodiazepine compounds described herein. The various benzodiazepine compounds are described more fully below. These compounds are therapeutically effective on their own, and have few or no toxic effects when administered in large doses. Further, as described in detail below, co-administration of these compounds with other agents provides an unexpected synergistic therapeutic benefit. In the co-administration methods, the claimed compounds are also useful in reducing deleterious side-effects of known therapeutic agents by decreasing the amount which must be administered to the subject.

The conditions which benefit from treatment with the compounds described herein appear to share the common etiology of dysregulation of the process of cell death. As described above in the Background, normal apoptosis occurs via several pathways, with each pathway having multiple steps. The methods described herein are useful in treating dysregulated apoptosis regardless of the pathway or the step in the pathway where the dysfunction is occurring. In one embodiment, the condition is caused as the result of dysregulation of the FAS apoptotic pathway. Similarly, the compounds are also useful in treating dysregulated necrosis regardless of the pathway or the step in the pathway where the dysfunction is occurring.

Dysregulation of the process of cell death is associated with many conditions. In neoplasms, for example, normal cell death is inhibited, allowing hyperproliferative growth of cells. Aberrant functioning of this process can also result in serious pathologies including autoimmune disorders, viral infections, conditions induced by viral infections, neurodegenerative disease, and the like. The present invention provides methods of treating these and other conditions. Without being bound by one theory, it seems that the effective compounds described herein induce or promote cell death in when this process is malfunctioning. Thus, in addition to treating conditions associated with dysregulation of apoptosis, the compounds of this invention also treat conditions in which there may not be any apoptotic defect. For example, in certain viral infections, while there may not be any apoptotic defect, cell death may be promoted by inducing necrosis.

The condition to be treated is generally determined by noting the presence of symptoms in the subject or by noting phenotypic or genotypic changes in the cells of the subject, in particular, the inability of the cell to undergo apoptosis or necrosis. Phenotypic changes associated with the neoplastic state of a cell (a set of in vitro characteristics associated with a tumorigenic ability in vivo) include more rounded cell morphology, looser substratum attachment, loss of contact inhibition, loss of anchorage dependence, release of proteases, increased sugar transport, decreased serum requirement, expression of fetal antigens, etc. See, Luria, et al., (1978) GENERAL VIROLOGY, 3rd edition, pp. 436–446 (John Wiley & Sons, New York). To "treat" as intended herein, means to induce cell death (wherein the cell death is either apoptotic or necrotic) in cells or tissue which are causative (primary or distal) of the disorder being treated. For example, in hyperproliferative disorders, the method will treat the disorder by inducing apoptosis of the hyperproliferative cells, such as neoplastic cells. In this embodiment, reduction in tumor size or tumor burden is one means to identify that the object of the method has been met. In other aspects, "to treat" encompasses restoration of immune function or regulation of immune dysfunction, as in autoimmune disorders and chronic inflammatory conditions. In other aspects, viral titer is eliminated or reduced in the subject being treated. In further aspects, "to treat" means to ameliorate the symptoms associated with a particular disease, e.g., cachexia in cancer or HIV infection or inflammation in arthritis. In still further aspects, prophylactic as well as therapeutic use of the compounds and methods of this invention are intended.

In the embodiment wherein the condition being treated is an autoimmune disease, the use of the methods disclosed herein will reduce autoantibody production and lead to a decrease in inflammation and tissue destruction. Thus, the cell that is being treated may be the cell that itself is autoimmunogenic or is affected distally by an autoimmune reaction, wherein it is desirable to induce cell death in such cells or tissue containing such cells. Similarly, in the case of treating inflammatory conditions, the cell that is being treated may be the inflammatory cell itself or is distally affected by inflammation wherein it is desirable to induce cell death in such cells or tissue containing such cells and thus reduce inflammation.

In a further embodiment, the cell being treated is a virally infected cell or a cell or tissue that previously has been infected. Successful therapy induces cell death and therefore a reduction in viral titer. This result is easily determined by assaying viral titer or by noting a reduction in cell number. It should be noted that, as can be inferred from the statements, supra, it may be desirable to induce cell death even among those cells that do not have any viral remnants or other signs of viral infections at the time of treatment because a viral infection that occurred much earlier in time could still cause disruption of cell death at a much later time.

Cell death may be assayed as described herein and in the art. Cell lines are maintained in appropriate culture conditions (e.g., gas ($CO_2$), temperature and media) and for an appropriate amount of time to attain exponential proliferation without density dependent constraints. Cell number and or viability may be measured using standard techniques, such as trypan blue exclusion/hemo-cytometry, or MTT dye conversion assay. Alternatively, the cell may be analyzed for the expression of genes or gene products associated with aberrations in apoptosis or necrosis.

It should be understood that the various dysregulatory disorders described above can be treated by any one or more of the benzodiazepine compounds, including the many alternative and specific embodiments presented herein. These benzodiazepines are described more fully below.

Antiviral Activity

In another embodiment, the compounds of the present invention may have antiviral activity independent of their efficacy to induce cell death. One aspect or method for inhibiting viral replication and/or propagation comprises contacting the virus with an effective amount of one or more compounds and/or compositions of the present invention. The contacting is conducted under suitable conditions to inhibit viral replication and/or propagation. In another aspect, the method comprises preventing viral infection and/or propagation in a cell or tissue by contacting the cell or tissue with an effective amount of the compounds and/or compositions as defined above. The contacting is conducted under suitable conditions to such that viral infection and/or propagation is inhibited.

The inhibition or prevention of viral infection, replication and/or propagation can be measured by assaying for viral titer, which methods are well known to those of skill in the art. By inhibiting and reducing viral replication and proliferation, viral infectivity also is inhibited and reduced and the host cells are suitably treated for viral infection with the additional benefit that associated pathologies also are treated.

As used herein, the term "suitable conditions" includes in vitro, ex vivo or in vivo conditions. These terms are well-known in the art.

The viruses that are contemplated under the present methods include RNA and/or DNA viruses. By way of example only, such viruses are of herpes, non-herpes and retroviral origins. Major examples of human pathogens of the herpes virus family include herpes simplex viruses (HSV) 1, 2, and cercopithecine herpes virus 1 (B-virus); varicella-zoster; Epstein-Barr virus (EBV); Lymphocryptovirus; human herpesviruses 6–8 (HHV6-S); kaposi-associated herpes virus (KHV); herpesvirus simiae, and human cytomegalovirus (HCMV). See, for example, Gallant, J. E. et al., *J. Infect. Dis.* 166:1223–1227, (1992).

Animal pathogens of herpesviral origin include infectious bovine rhinotracheitis virus, bovine mammillitis virus, and cercopithecine herpesvirus (B-virus), among others.

The human viruses of non-herpes origin include influenza viruses A, B and C; parainfluenza viruses —1, 2, 3 and 4; adenovirus; reovirus; respiratory syncytial virus; rhinovirus; coxsackle virus; echo virus; rubeola virus; hepatitis viruses of the types B and C (HBV and HCV); and papovavirus.

The animal viruses of non-herpes origin include pseudorabies virus (PRV, of swine), equine rhinopneumonitis, coital exanthema viruses (varicella viruses); lymphocryptovirus; Marek's disease virus, Bovine Herpesvirus-1 (BHV-1), herpesvirus Pseudorabies virus (PRV).

The viruses of retroviral origin that are contemplated to be treatable by the compounds and compositions of this invention include human immunodeficiency viruses (HIV) of the types 1 and 2 and human lymphotropic 1 and 2 viruses (HTLV-I and II).

D. Methods of Identifying Potential Therapeutic Agents

Also provided herein is an assay to identify a potential agent to treat a condition associated with the dysregulation of the apoptotic or necrotic pathway. The method comprises contacting the dysregulated cell, i.e., a cell affected by the disorder (e.g., a tumor cell when the condition is hyperproliferative) or an immune cell (a neutrophil, basophil, eosinophil, monocyte, or lymphocyte) when the condition is a chronic inflammatory condition or an autoimmune disorder) with the agent. In a further aspect of this invention, a control cell is further assayed with or without a benzodiazepine compound. The benzodiazepine compound may be a 1,4-benzodizepine compound as described herein. Cell death as compared to the control cell is also noted and compared. To identify these potential therapeutic agents, appropriate assay conditions (e.g., incubation time, temperature, culture maintenance medium, etc.) can be readily determined by one of skill in the art. Serum may be obtained from any commercial source, for example, fetal bovine serum from Gibco BRL (Gaithersburg, Md.). The cells are cultured with the test agent for a sufficient amount of time. Following the appropriate incubation period, cell death may then be assayed by any means described above, for example by MTT dye trypan exclusion. Thus, novel cytotoxic agents can be identified by their ability to induce cell death to the dysregulated cells. Further, comparisons can also be made to cell death in control cells.

The present inventors have discovered that when the cells are maintained in low serum conditions, cytotoxicity is greatly exacerbated and the incubation time is reduced to about 2 hours or less. This is quite an unexpected result since under standard incubation conditions, which employ higher serum levels, the required incubation time is often several hours, approaching in some cases 24 hours or more. "Low serum" as used herein refers to culture media containing less than about 10% per volume down to or equal to less than about 0.1% (v/v). It should be understood that within this range the concentration is flexible, and the applicants contemplate any possible subrange in increments of about 0.1% within this range, for example, less than or equal to about any of 0.1, 0.2, 0.3, 0.4, 0.5, 0.6, 0.7, 0.8, . . . 1.0, . . . 1.5, . . . 2.0, . . . 2.5, . . . 3.0, . . . 3.5, . . . 5%, etc., to about 9.9, and to about 10% of serum (% v/v).

Thus, in one aspect, the benzodiazepines of this invention induce apoptosis in low serum as defined above.

In a further aspect, the benzodiazepines of this invention are further characterized and identified by their lack of ability to bind to a central benzodiazepine receptor or to bind with low affinity to a peripheral benzodiazepine receptor. These compounds can be identified by using methods well-known in the art.

For example, the binding affinity of a benzodiazepine compound for a peripheral benzodiazepine receptor can be determined according to well-established methodology as described in Schoemaker, H. et al. (1983) *J. Pharm. Exp Ther.* 225:61–69; and Doble, A. et al. (1987) *Brain Res. Bull.* 18:49–61.

Briefly, the method comprises comparing the potency of a benzodiazepine compound with that of a well-known high affinity binding agent such as 1-(2-chlorophenyl)-N-methyl-N-(-1, methylpropyl)-3-isoquinolinecarboxamide (PK11195), wherein the ability of the benzodiazepine compound to displace PK511195 from the peripheral benzodiazepine receptors in a competitive binding assay.

In any of the above assay methods, the benzodiazepine compound can be detectably labeled. Such detectable labeling includes labeling with an isotope or with a fluorescing moiety. Examples of isotope labeling include usage of stable or radioactive isotopes of one or more atoms on the benzodiazepine molecule.

Methods for introducing such detectable labels and for detecting the labels are well-known in the art. For example, the radioisotope label can be detected using special instrumentation, including electron spin resonance spectrometers. The stable isotopes can be detected using mass spectrometers, or magnetic resonance spectrometers. The fluorescent labels can be detected using fluorescent spectrometers. Many of these instruments are commercially available and their operation is within the ordinary skill in the art.

The benzodiazepine compounds that can be used in the assay and diagnostic methods are described in greater detail below. It should be understood that all the compounds described therein, including the many general and specific embodiments, can be used in the assay and diagnostic methodology.

E. Use of Benzodiazepine Compounds for Preparing Medicaments

The benzodiazepine compounds of the present invention are also useful in the preparation of medicaments to treat a variety of conditions associated with dysregulation of cell death as described above. In addition, the compounds can also be used to prepare medicaments for treating other disorders wherein the effectiveness of the benzodiazepines are known or predicted. Such disorders may include neurological or neuromuscular disorders. The methods and techniques for preparing medicaments of a compound are well-known in the art. Some possible pharmaceutical formulations and routes of delivery are detailed below.

Thus, one of skill in the art would readily appreciate that any one or more of the compounds described more fully below, including the many specific embodiments, can be used by applying standard pharmaceutical manufacturing procedures to prepare medicaments to treat the many disorders described herein above. Such medicaments can be delivered to the subject by using delivery methods that are well-known in the pharmaceutical arts.

F. Compositions and Formulations

While it is possible for the agent to be administered alone, it is preferable to present it as a pharmaceutical formulation comprising at least one active ingredient, as defined above, together with a solid support or alternatively, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets maybe made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, paste, gel, spray, aerosol or oil. Alternatively, a formulation may comprise a patch or a dressing such as a bandage or adhesive plaster impregnated with active ingredients, and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the agent through the skin or other affected areas. Examples of such dermal penetration enhancers include dimethylsulfoxide (DMSO) and related analogues.

The oily phase of the emulsions of this invention may be constituted from known ingredients in an known manner. While this phase may comprise merely an emulsifier (otherwise known as an emulgent), it desirably comprises a mixture of at least one emulsifier with a fat or an oil or with both a fat and an oil.

Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

G. Pharmaceutical Delivery

Various delivery systems are known and can be used to administer a therapeutic agent of the invention, e.g., encapsulation in liposomes, microparticles, microcapsules, receptor-mediated endocytosis (see, e.g., Wu and Wu, (1987), *J. Biol. Chem.* 262:4429–4432), and the like. Methods of delivery include but are not limited to, intra-arterial, intramuscular, intravenous, intranasal, and oral routes. In a specific embodiment, it may be desirable to administer the pharmaceutical compositions of the invention locally to the area in need of treatment; this may be achieved by, for example, and not by way of limitation, local infusion during surgery, by injection, or by means of a catheter.

The agents identified herein as effective for their intended purpose can be administered to subjects or individuals susceptible to or at risk of developing a condition correlated with dysregulation of the apoptotic or necrotic pathway. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts can be empirically determined and will vary with the pathology being treated, the subject being treated and the efficacy and toxicity of the agent. When delivered to an animal, the method is useful to further confirm efficacy of the agent. One example of an animal model is MLR/MpJ-lpr/lpr ("MLR-lpr") (available from Jackson Laboratories, Bal Harbor, Me.). MLR-lpr mice develop systemic autoimmune disease. Alternatively, other animal models can be developed by inducing tumor growth, for example, by subcutaneously inoculating nude mice with about $10^5$ to about $10^9$ hyperproliferative, cancer or target cells as defined herein. When the tumor is established, the compounds described herein are administered, for example, by subcutaneous injection around the tumor. Tumor measurements to determine reduction of tumor size are made in two dimensions using venier calipers twice a week. Other animal models may also be employed as appropriate. Such animal models for the above-described diseases and conditions are well-known in the art. See, for example, (1992) *Am. J. Pathol.* 36:875–882.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician.

Suitable dosage formulations and methods of administering the agents can be readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

H. Co-Administration

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is hyperproliferation, the additional agent can be a chemotherapeutic agent or radiation. When the condition being treated is an autoimmune disorder, the additional agent can be an immunosuppressant or an anti-inflammatory agent. When the condition being treated is chronic inflammation, the additional agent can be an anti-inflammatory agent. When the condition being treated is a viral infection or conditions induced by a viral infection, the additional agent can be an antiviral agent. The additional agents to be co-administered, such as anticancer, immunosuppressant, anti-inflammatory, and antiviral agents can be any of the well-known agents in the art, including those that are currently in clinical use. The determination of appropriate type and dosage of radiation treatment is also within the skill in the art or can be determined with relative ease.

Currently, treatment of the various conditions associated with abnormal apoptosis is limited by the following two major factors: (1) the development of drug resistance and (2) the toxicity of known therapeutic agents. In certain cancers, for example, resistance to chemicals and radiation therapy has been shown to be associated with inhibition of apoptosis. See, Desoize, B. (1994) *Anticancer Res.* 14:2291–2294. Similarly, some therapeutic agents have deleterious side effects, including non-specific lymphotoxicity, renal and bone marrow toxicity.

The methods described herein address both these problems. Drug resistance, where increasing dosages are required to achieve therapeutic benefit, is overcome by co-administering the compounds described herein with the known agent. The compounds described herein appear to sensitize target cells to known agents and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases were drug resistance has increased the requisite dosage. When the claimed compounds are co-administered with the known agent, they reduce the dosage required which, in turn, reduces the deleterious effects. Further, because the claimed compounds are themselves both effective and non-toxic in large doses, co-administration of proportionally more of these compounds than known toxic therapeutics will achieve the desired effects while minimizing toxic effects.

I. The Benzodiazepine Compounds

The compounds of the present invention are benzodiazepine compounds. In some aspects, the benzodiazepine compounds have the following structure:

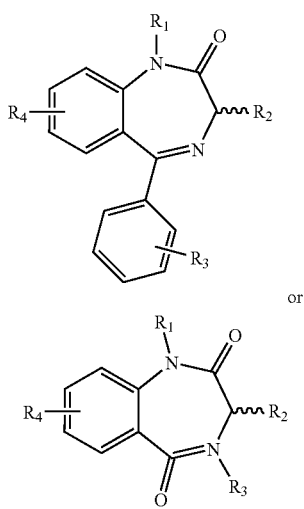

or its enantiomer,
wherein,
$R_1$ is aliphatic or aryl;
$R_2$ is aliphatic, aryl, —NH$_2$, —NHC(=O)—R$_5$, or a moiety that participates in hydrogen bonding,
wherein $R_5$ is aryl, heterocyclic, —R$_6$—NH—C(=O)—R$_7$ or —R$_6$—C(=O)—NH—R$_7$, wherein $R_5$ is an aliphatic linker of 1–6 carbons and $R_7$ is aliphatic, aryl, or heterocyclic,
each of $R_3$ and $R_4$ is independently a hydroxy, alkoxy, halo, amino, lower-alkyl-substituted-amino, acetylamino, hydroxyamino, an aliphatic group having 1–8 carbons and 1–20 hydrogens, aryl, or heterocyclic;
or a pharmaceutically acceptable salt, prodrug or derivative thereof.

In the above structures, $R_1$ is a hydrocarbyl group of 1–20 carbons and 1–20 hydrogens. Preferably, $R_1$ has 1–15 carbons, and more preferably, has 1–12 carbons. Preferably, $R_1$ has 1–12 hydrogens, and more preferably, 1–10 hydrogens. Thus $R_1$ can be an aliphatic group or an aryl group.

The term "aliphatic" represents the groups commonly known as alkyl, alkenyl, alkynyl, alicyclic. The term "aryl" as used herein represents a single aromatic ring such as a phenyl ring, or two or more aromatic rings that are connected to each other (e.g., bisphenyl) or fused together (e.g., naphthalene or anthracene). The aryl group can be optionally substituted with a lower aliphatic group (e.g., $C_1$–$C_4$ alkyl, alkenyl, alkynyl, or $C_3$–$C_6$ alicyclic). Additionally, the aliphatic and aryl groups can be further substituted by one or more functional groups such as —NH$_2$, —NHCOCH$_3$, —OH, lower alkoxy ($C_1$–$C_4$), halo (—F, —Cl, —Br, or —I). It is preferable that $R_1$ is primarily a nonpolar moiety.

In the above structures, $R_2$ can be aliphatic, aryl, —NH$_2$, —NHC(=O)—R$_5$, or a moiety that participates in hydrogen bonding, wherein $R_5$ is aryl, heterocyclic, R$_6$—NH—C(=O)—R$_7$ or —R$_6$—C(=O)—NH—R$_7$, wherein $R_6$ is an aliphatic linker of 1–6 carbons and $R_7$ is an aliphatic, aryl, or heterocyclic. The terms "aliphatic" and "aryl" are as defined above.

The term "a moiety that participates in hydrogen bonding" as used herein represents a group that can accept or donate a proton to form a hydrogen bond thereby. Some specific nonlimiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups ($C_1$–$C_4$) to which the respective oxygen-containing functional group is attached. Thus, for example, the term "lower carbonyl" refers to inter alia, formaldehyde, acetaldehyde.

Some nonlimiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups.

It is also possible that the hydrogen-bond acceptor in the present invention can be the π electrons of an aromatic ring. However, the hydrogen bond participants of this invention do not include those groups containing metal atoms such as boron. Further the hydrogen bonds formed within the scope of practicing this invention do not include those formed between two hydrogens, known as "dihydrogen bonds." See, Crabtree, R. H. (1998) *Science* 282:2000–2001, for further description of such dihydrogen bonds.

The term "heterocyclic" represents a 3–6 membered aromatic or nonaromatic ring containing one or more heteroatoms. The heteroatoms can be the same or different from each other. Preferably, at least one of the heteroatoms is nitrogen. Other heteroatoms that can be present on the heterocyclic ring include oxygen and sulfur.

Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine.

Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine.

Examples of heterocyclic rings containing two different heteroatoms include, but are not limited to, phenothiazine, morpholine, parathiazine, oxazine, oxazole, thiazine, and thiazole.

The heterocyclic ring is optionally further substituted with one or more groups selected from aliphatic, nitro, acetyl (i.e., —C(=O)—CH$_3$), or aryl groups.

Each of $R_3$ and $R_4$ can be independently a hydroxy, alkoxy, halo, amino, or substituted amino (such as loweralkyl-substituted-amino, or acetylamino or hydroxyamino), or an aliphatic group having 1–8 carbons and 1–20 hydrogens. When each of $R_3$ and $R_4$ is an aliphatic group, it can be further substituted with one or more functional groups such as a hydroxy, alkoxy, halo, amino or substituted amino groups as described above. The terms "aliphatic" is defined above. Alternatively, each of $R_3$ and $R_4$ can be hydrogen.

It is well-known that many 1,4-benzodiazepines exist as optical isomers due to the chirality introduced into the heterocyclic ring at the $C_3$ position. The optical isomers are sometimes described as L- or D-isomers in the literature. Alternatively, the isomers are also referred to as R- and S-enantiomorphs. For the sake of simplicity, these isomers are referred to as enantiomorphs or enantiomers. The 1,4-benzodiazepine compounds described herein include their enantiomeric forms as well as racemic mixtures. Thus, the usage "benzodiazepine or its enantiomer" herein refers to the benzodiazepine as described or depicted, including all its enantiomorphs as well as their racemic mixture.

From the above description, it is apparent that many specific examples are represented by the generic formulas presented above. Thus, in one example, $R_1$ is aliphatic, $R_2$ is aliphatic, whereas in another example, $R_1$ is aryl and $R_2$ is a moiety that participates in hydrogen bond formation. Alternatively, $R_1$ can be aliphatic, and $R_2$ can be an —NHC(=O)—$R_5$, or a moiety that participates in hydrogen bonding, wherein R is aryl, heterocyclic, —$R_6$—NH—C(=O)—$R_7$ or —$R_6$—C(=O)—NH—$R_7$, wherein $R_6$ is an aliphatic linker of 1–6 carbons and $R_7$ is an aliphatic, aryl, or heterocyclic. A wide variety of such combinations arising from selecting a particular group at each substituent position are possible and all such combinations are within the scope of this invention.

Further, it should be understood that the numerical ranges given throughout this disclosure should be construed as a flexible range that contemplates any possible subrange within that range. For example, the description of a group having the range of 1–10 carbons would also contemplate a group possessing a subrange of, for example, 1–3,1–5, 1–8, or 2–3, 2–5, 2–8, 3–4, 3–5, 3–7, 3–9, 3–10, etc., carbons. Thus, the range 1–10 should be understood to represent the outer boundaries of the range within which many possible subranges are clearly contemplated. Additional examples contemplating ranges in other contexts can be found throughout this disclosure wherein such ranges include analogous subranges within.

Some specific examples of the benzodiazepine compounds of this invention include:

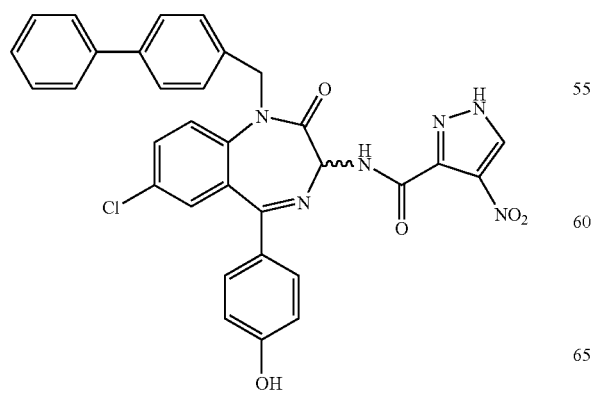

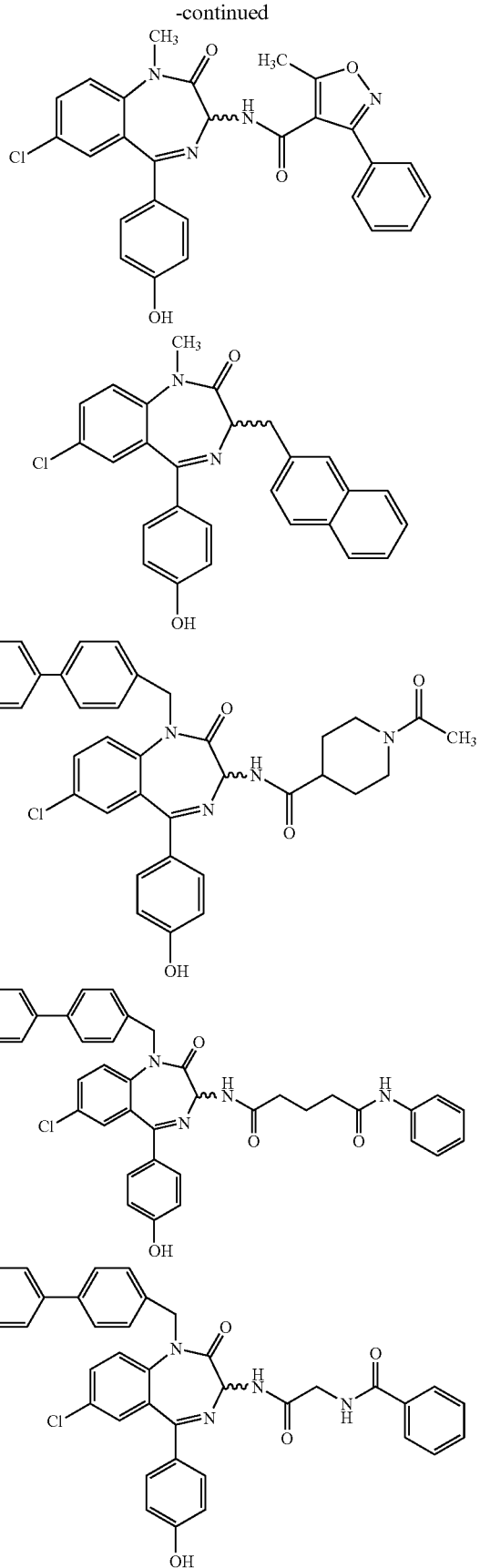

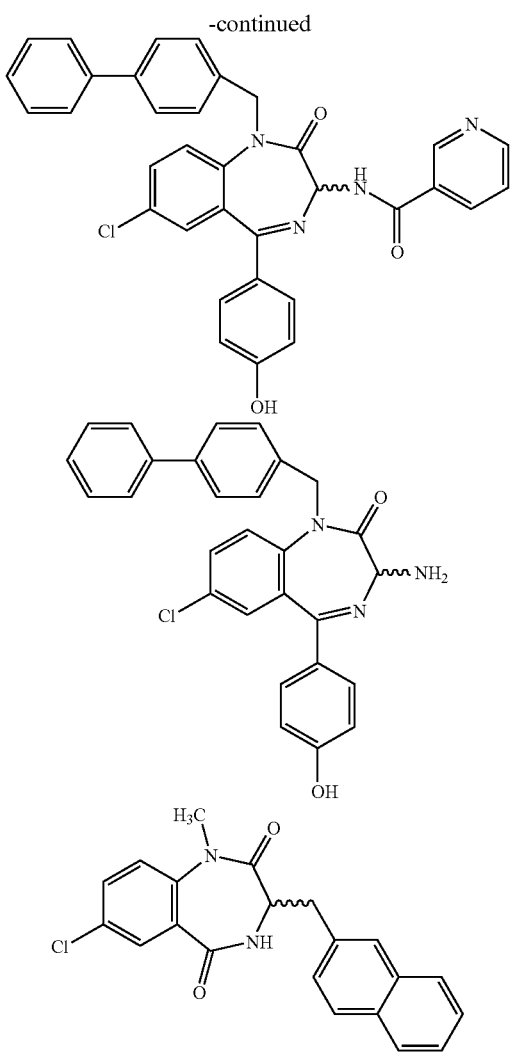

In summary, several benzodiazepine compounds are presented herein. Any one or more of these benzodiazepine compounds can be used to treat a variety of dysregulatory disorders related to cellular death. Such disorders include autoimmune disorders, inflammatory conditions, hyperproliferative conditions, viral infections, and atherosclerosis. In addition, the above compounds can be used to prepare medicaments to treat the above-described dysregulatory disorders. The above-described benzodiazepines can also be used in drug screening assays and other diagnostic methods. The broad scope of the methodology, uses and compositions described herein becomes readily apparent from a comprehensive reading of the entire description, noting that preferred and advantageous features of some aspects are applicable to other aspects of the invention.

J. Preparation of Compounds

The above-described benzodiazepine compounds can be prepared using either solid-phase or soluble-phase combinatorial synthetic methods as well as on an individual basis from well-established techniques. See, for example, Boojamra, C. G. et al. (1996) *J. Org. Chem.* 62:1240–1256; Bunin, B. A., et al. (1994) *Proc. Natl. Acad. Sci. USA* 91:4708–4712; Stevens, S. Y. et al., (1996) *J. Am. Chem. Soc.* 118:10650–10651; Gordon, E. M., et al., (1994) *J. Med. Chem.* 37:(10)1385–1401; and U.S. Pat. Nos. 4,110,337 and 4,076,823, which are all incorporated by reference herein. For illustration, the following general methodologies are provided.

1. Preparation of 1.4-benzodiazepine-2-one compounds

Improved solid-phase synthetic methods for the preparation of a variety of 1,4-benzodiazepine-2-one derivatives with very high overall yields have been reported in the literature. See, for example, Bunin and Ellman ((1992) *J. Am. Chem. Soc.* 114:10997–10998). Using these improved methods, the 1,4-benzodiazepine-2-ones can be constructed on a solid support from three separate components: 2-aminobenzophenones, α-amino acids, and (optionally) alkylating agents, as shown in the reaction scheme of FIG. 1.

Preferred 2-aminobenzophenones include the substituted 2-aminobenzophenones, for example, the halo-, hydroxy-, and halo-hydroxy-substituted 2-aminobenzophenones, such as 4-halo-4'-hydroxy-2-aminobenzophenones. A preferred substituted 2-aminobenzophenone is 4-chloro-4'-hydroxy-2-aminobenzophenone. Preferred α-amino acids include the 20 common naturally occurring α-amino acids as well as α-amino acid mimicking structures, such as homophenylalanine, homotyrosine, and thyroxine.

Alkylating agents include both activated and inactivated electrophiles, of which a wide variety are well known in the art. Preferred alkylating agents include the activated electrophiles p-bromobenzyl bromide and t-butyl-bromoacetate.

In the first step of such a synthesis, the 2-aminobenzophenone derivative, (1) of FIG. 1, is attached to a solid support, such as a polystyrene solid support, through either a hydroxy or carboxylic acid functional group using well known methods and employing an acid-cleavable linker, such as the commercially available [4-(hydroxymethyl)phenoxy]acetic acid, to yield the supported 2-aminobenzophenone, (2). See, for example, Sheppard and Williams, ((1982)) *Int. J. Peptide Protein Res.* 20:451–454). The 2-amino group of the aminobenzophenone is preferably protected prior to reaction with the linking reagent, for example, by reaction with FMOC-Cl (9-fluorenylmethyl chloroformate) to yield the protected amino group 2'-NHFMOC.

In the second step, the protected 2-amino group is deprotected (for example, the —NHFMOC group may be deprotected by treatment with piperidine in dimethylformamide (DMF)), and the unprotected 2-aminobenzophenone is then coupled via an amide linkage to an α-amino acid (the amino group of which has itself been protected, for example, as an —NHFMOC group) to yield the intermediate (3). Standard activation methods used for general solid-phase peptide synthesis may be used (such as the use of carbodiimides and hydroxybentzotriazole or pentafluorophenyl active esters) to facilitate coupling. However, a preferred activation method employs treatment of the 2-aminobenzophenone with a methylene chloride solution of the of α-N-FMOC-amino acid fluoride in the presence of the acid scavenger 4-methyl-2,6-di-tert-butylpyridine yields complete coupling via an amide linkage. This preferred coupling method has been found to be effective even for unreactive aminobenzophenone derivatives, yielding essentially complete coupling for derivatives possessing both 4-chloro and 3-carboxy deactivating substituents.

In the third step, the protected amino group (which originated with the amino acid) is first deprotected (for example, —NHFMOC may be converted to —NH₂ with piperidine in DMF), and the deprotected compound is reacted with acid, for example, 5% acetic acid in DMF at 60° C., to yield the supported 1,4-benzodiazepine derivative, (4). Complete cyclization has been reported using this method for a variety of 2-aminobenzophenone derivatives with widely differing steric and electronic properties.

In an optional fourth step, the 1,4-benzodiazepine derivative may be alkylated, by reaction with a suitable alkylating agent and a base, to yield the supported fully derivatized 1,4-benzodiazepine, (5). Standard alkylation methods, for example, an excess of a strong base such as LDA (lithium diisopropylamide) or NaH, may be used; however, such methods may result in undesired deprotonation of other acidic functionalities and over-alkylation. Preferred bases, which may prevent over-alkylation of the benzodiazepine derivatives (for example, those with ester and carbamate functionalities), are those which are basic enough to completely deprotonate the anilide functional group, but not basic enough to deprotonate amide, carbamate or ester functional groups. An example of such a base is lithiated 5-(phenylmethyl)-2-oxaxolidinone, which may be reacted with the 1,4-benzodiazepine in tetrahydrofuran (THF) at −78° C. Following deprotonation, a suitable alkylating agent, as described above, is added.

In the final step, the fully derivatized 1,4-benzodiazepine, (6), is cleaved from the solid support. This may be achieved (along with concomitant removal of acid-labile protecting groups), for example, by exposure to a suitable acid, such as a mixture of trifluoroacetic acid, water, and dimethylsulfide (85:5:10, by volume). Alternatively, the above benzodiazepines can be prepared in soluble phase. The synthetic methodology was outlined by Gordon et al. (1994) *J. Med. Chem.* 37:1386–1401, which is hereby incorporated by reference. Briefly, the methodology comprises trans-imidating an amino acid resin with appropriately substituted 2-aminobenzophenone imines to form resin-bound imines. These imines can be cyclized and tethered by procedures similar to those in solid-phase synthesis described above. The general purity of benzodiazepines prepared using the above methodology can be about 90% or higher.

2. Preparation of 1,4-benzodiazepine-2,5-diones

Figure 2:
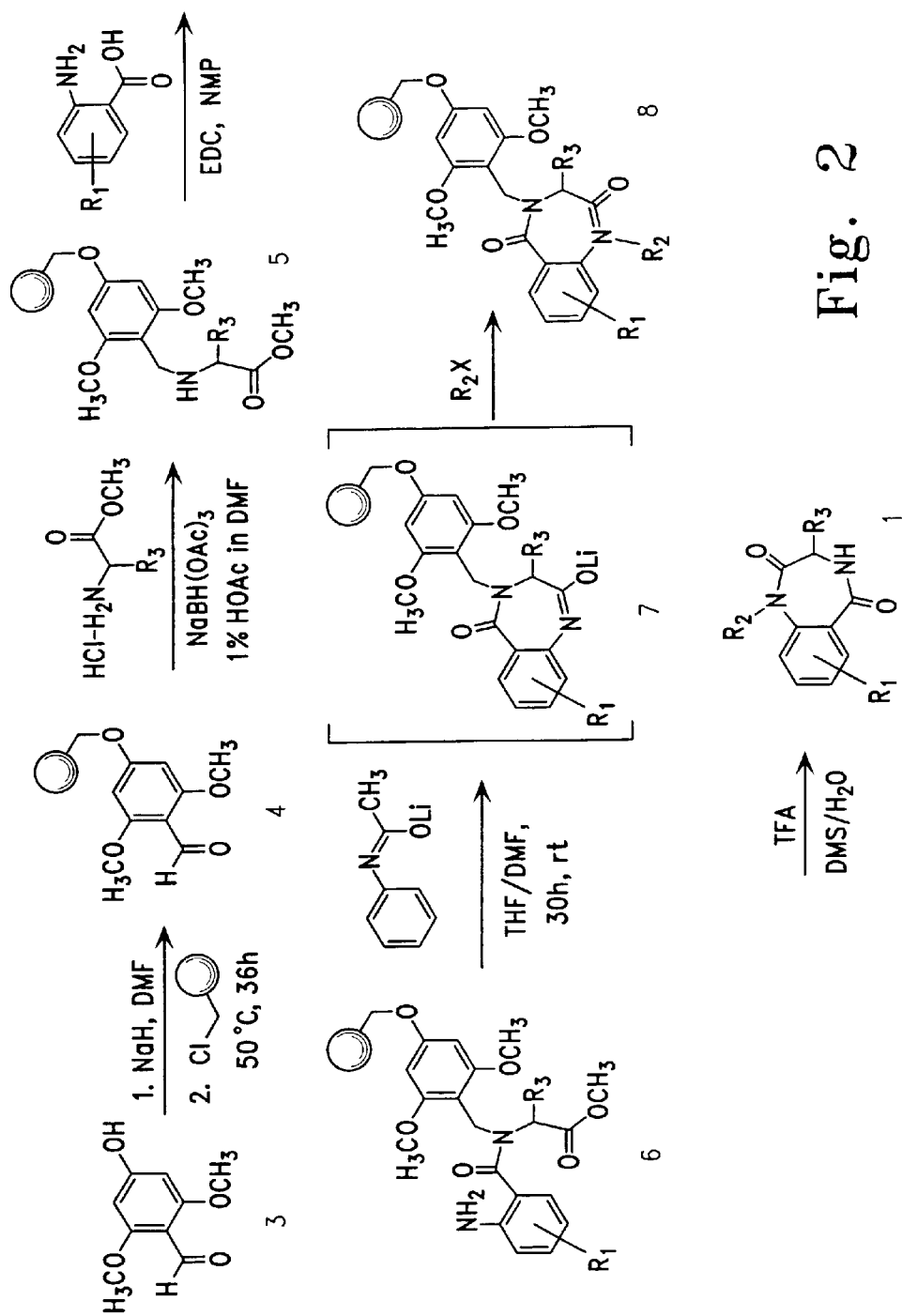
FIG. 2 shows a general synthetic scheme for solid-phase synthesis of 1,4-benzodiazepine-2,5-dione compounds of the present invention.

A general method for the solid-phase synthesis of 1,4-benzodiazepine-2,5-diones has been reported in detail by Boojamra, C. J. et al. (1996) *J. Org. Chem.* 62:1240–1256. This method can be used to prepare the compounds of the present invention. This method is depicted in FIG. 2.

Briefly, a Merrifield resin, for example, a (chloromethyl) polystyrene is derivatized by alkylation with 4-hydroxy-2,6-dimethoxybenzaldehyde sodium (3) to provide resin-bound aldehyde (4). An α-amino ester is then attached to the derivatized support by reductive amination using NaBH(OAc)$_3$ in 1% acetic acid in DMF. This reductive amination results in the formation of a resin-bound secondary amine (5).

The secondary amine (5) is acylated with a wide variety of unprotected anthranilic acids result in support-bound tertiary amides (6). This acylation can be best achieved by performing the coupling reaction in the presence of a carbodiimide and the hydrochloride salt of a tertiary amine. One good such coupling agent is 1-ethyl-8-[8-(dimethylamino)propyl] carbodiimide hydrochloride. The reaction is typically performed in the presence of anhydrous 1-methyl-2-pyrrolidinone. The coupling procedure can be repeated once more to ensure complete acylation.

Cyclization of the acyl derivative (6) can be accomplished through base-catalyzed lactamation through the formation of an anilide anion (7) which would react with an alkylhalide for simultaneous introduction of the substituent at the 1-position on the nitrogen of the heterocyclic ring of the benzodiazepine. The lithium salt of acetanilide is a good base to catalyze the reaction. Thus, (6) can be reacted with lithium acetanilide in DMF/THF (1:1) for 30 hours followed by reaction with appropriate alkylating agent provides the fully derivatized support-bound benzodiazepine (8). The compounds (1) can be cleaved from the support in good yield and high purity by using TFA/DMS/H$_2$O (90:5:5).

Some examples of the α-amino ester starting materials, alkylating agents, and anthranilic acid derivatives that can be used in the present invention are listed by Boojamra, supra at 1246. Additional reagents can be readily determined and either can be commercially obtained or readily prepared by one of ordinary skill in the art to arrive at the novel substituents disclosed in the present invention.

For example, from FIG. 2, and from Boojamra, supra, one realizes that: alkylating agents provide the $R_1$ substituents; α-amino ester starting materials provide the $R_2$ substituents, and anthranilic acids provide the $R_4$ substituents. By employing these starting materials that are appropriately substituted, one arrives at the desired 1,4-benzodiazepine-2,5-dione. The $R_3$ substituent can be obtained by appropriately substituting the amine of the α-aminoester starting material. If steric crowding becomes a problem, the $R_3$ substituent can be attached through conventional methods after the 1,4-benzodiazepine-2,5-dione is isolated.

3. Chirality

It should be recognized that many of the benzodiazepines of the present invention can exist as optical isomers due to chirality wherein the stereocenter is introduced by the α-amino acid and its ester starting materials. The above-described general procedure preserves the chirality of the α-amino acid or ester starting materials. In many cases such preservation of chirality is desirable. However, when the desired optical isomer of the α-amino acid or ester starting material is unavailable or expensive, a racemic mixture can be produced which can be separated into the corresponding optical isomers and the desired benzodiazepine enantiomer can be isolated.

For example, in the case of the 2,5-dione compounds, Boojamra, supra, discloses that complete racemization can be accomplished by preequilibrating the hydrochloride salt of the enantiomerically pure α-amino ester starting material with 0.3 equivalents of i-Pr$_2$EtN and the resin-bound aldehyde for 6 hours before the addition of NaBH(OAc)$_3$. The rest of the above-described synthetic procedure remains the same. Similar steps can be employed, if needed, in the case of the 1,4-benzodiazepine-2-dione compounds as well.

Methods to prepare individual benzodiazepines are well-known in the art. See for example, U.S. Pat. Nos. 3,415,814; 3,384,635; and 3,261,828, which are hereby incorporated by reference. By selecting the appropriately substituted starting materials in any of the above-described methods, the benzodiazepines of this invention can be prepared with relative ease.

From the above description of the invention, one of skill in the art readily understands that the various methods of treatment, diagnostic methods, use of compounds to prepare medicaments, delivery of such medicaments, and the making of the compounds, can be practiced in many different ways. It is also understood that preferred features and characteristics of one aspect of the invention are applicable to any other aspect of the invention. In addition, the disclosure of this invention, coupled with the ordinary skill in the art can lead to further treatments, diagnostic methods, uses, formulations and compositions. Such further treatments, diagnostic methods, uses, formulations, and compositions are within the scope of this invention, which scope is thus considerably broader than the many examples presented herein, including the ones presented below.

EXAMPLES

General Methods

Cell Preparation

Cell lines were cultured in complete media (RPMI or DMEM containing 10% fetal bovine serum supplemented with penicillin, streptomycin, and L-glutamine) at 37° C., 5% $CO_2$. For activity assays, cells in log-phase growth were removed and diluted to a concentration between 100,000 and 300,000/mL. Some cells were kept in complete media, while an identical aliquot was exchanged into reduced serum media (RPMI or DMEM containing 0.2% fetal bovine serum supplemented with penicillin, streptomycin, and L-glutamine) by centrifugation.

Activity Assay

Cells in both complete media and reduced serum media were dispensed into 96 well plates in 100 μL aliquots giving 10,000 to 30,000 cells/well. Compound was then added to appropriate wells in the plate (2 μL of each 50× stock) at concentrations between 1 nM to 20 μM. Cells were then cultured overnight 37° C., 5% $CO_2$). Relative cell number/cell viability was measured using standard techniques (trypan blue exclusion/hemocytometry, MTT dye conversion assay).

Example 1

Ability to Induce Cell Death

Several individual representative compounds that induce apoptosis have been shown above. Of these, the most potent compound is identified as Compound 1, which is shown below.

Compound I

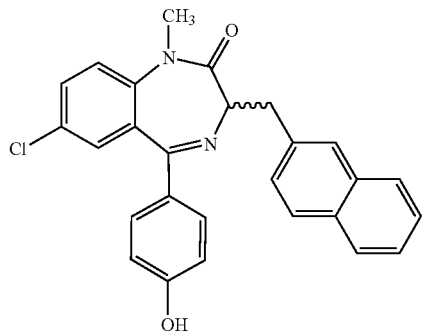

Compound 1 was used to induce cell death in a variety of cells by using the above-described materials and methods. Table 1 shows cell viability data after 18 hours of culture with Compound 1 in reduced serum media as described above.

TABLE 1

| Cell Line | Source | Type | 4 μM Bz | 6 μM Bz | 10 μM Bz |
|---|---|---|---|---|---|
| Jurkat | human | T-cell | 0 | 0 | 0 |
| IMR | human | neuroblastoma | 100 | 0 | 0 |
| SHSY-5Y | human | neuroblastoma | Nd | 0 | 0 |
| Shep | human | neuroblastoma | Nd | 80 | 0 |
| 293T | human | Embryonic fibroblast | Nd | Nd | 30 |
| RAW 246.7 | murine | monocytic | 70% | 0 | 0 |
| NIH 3T3 | murine | fibroblast | Nd | Nd | 25 |

(lower numbers equal increased killing).
Nd = Not determined

Example 2

MRL/MpJ-lpr/lpr(MRL-lpr) mice develop similar serological and histological manifestations of autoimmune disease as human SLE. These mice were developed by a series of cross-breeding of inbred strains until an autoimmune phenotype appeared. (Theofilopoulos A. N. and Dixon F. J. (1985) *Adv. Immunol.* 37:269–390). The MRL-lpr mice are characterized by the spontaneous development of systemic autoimmune disease. This disease is manifested in several physiological locations and resembles a variety of human diseases. For instance, the kidney damage in these mice is associated with high serological titers of anti-DNA as in human SLE. They also develop an erosive arthropathy and a lymphocytic infiltration of the salivary glands, similar to the human diseases rheumatoid arthritis (RA) and Sjörgen's disease, respectively (Theofilopoulos, supra).

In general MRL-lpr mice have a profound defect in apoptosis due the mutation of the lpr gene locus. (Sakata K. et al. (1998) *Clin. Immunol. Immunopathol.* 87:1–7). The defect has been linked to a mutation in the Fas receptor gene, important in the signaling of apoptosis in activated lymphocytes. (Watanabe-Fukunaga, R. et al. (1992) *Nature* 356:314–317). Consequently, these mice show a profound lymphoproliferation resulting in massive enlargement of the lymph nodes and spleen. Grossly, these mice demonstrate swollen footpads and erythematous skin lesions. Histologically, glomerulonephritis, arthritis, and inflammatory infiltration of the salivary glands are notable.

Methods

Mice

Six week old, female MRL-lpr mice were purchased from Jackson Laboratories (Bal Harbor, Me.). The animals were allowed to adapt to their environment for one week prior to commencement of the treatment study. The mice were housed in a climate controlled specific pathogen-free environment on a 12 hour light dark cycle with food and water ad libitum. Once a week, weights were measured and proteinuria was examined using a colorimetric reaction (Boehringer Mannheim ChemStrip 6).

Treatment Regimen

Mice were randomized into three groups: controls receiving PBS (50 μL, qod), controls receiving DMSO (50 μL, qod), and mice receiving Compound 1 in 50 μL of DMSO (60 mg/kg qod ip for 20 mice and 30 mg/kg qod ip for 10 mice). Intraperitoneal injections were given with a 30 G needle and glass syringes (Hamilton) on an every other day dosing schedule. Treatment started at 7 weeks of age for the control mice (those receiving PBS and DMSO) and at 8 or 9 weeks for the treatment mice. At the end of the study, blood was collected by tail bleeds. The mice were subsequently anesthetized by metophane inhalation and were sacrificed by exsanguination by axillary dissection. Sample organs were then removed for histological analysis.

Statistical Analysis

Analysis of statistical significance was done using the computer program SPSS. Unless otherwise noted, the Mann-Whitney U test (one-tailed) was used and probability values >5% were considered insignificant.

Results

Disease Progression

MRL-lpr mice are known to develop a kidney disease very similar to that seen in the human autoimmune disease Systemic Lupus Erythematosus (SLE). The hallmark of this disease is a glomerulonephritis that results in loss of kidney function and eventual death due to kidney failure. A marker for the development of kidney disease is the amount of protein present in the urine. As kidney function deteriorates, the glomerular filtration mechanism fails and proteinuria increases. Unlike the periodicity of the human disease, the murine form of lupus is progressive; thus, once a mouse develops nephritis and the ensuing proteinuria the disease progresses on a continuum until death. This allows the use of proteinuria measurements to follow the progression of kidney disease in the MRL-lpr mice.

The development of disease in our study was followed by weekly measurement of the proteinuria. Any given mouse was determined to have lupus if she had proteinuria values >2+(>100 mg/dL) for 2 or more consecutive weeks. No mice meeting this criterion were ever found to have drops in proteinuria below 2+. Furthermore, the mice that died with >2+ proteinuria were found to have very significant glomerulonephritis and the mice that died with values <2+ had healthy kidneys and causes of death unrelated to the autoimmune disease.

Figure 3:
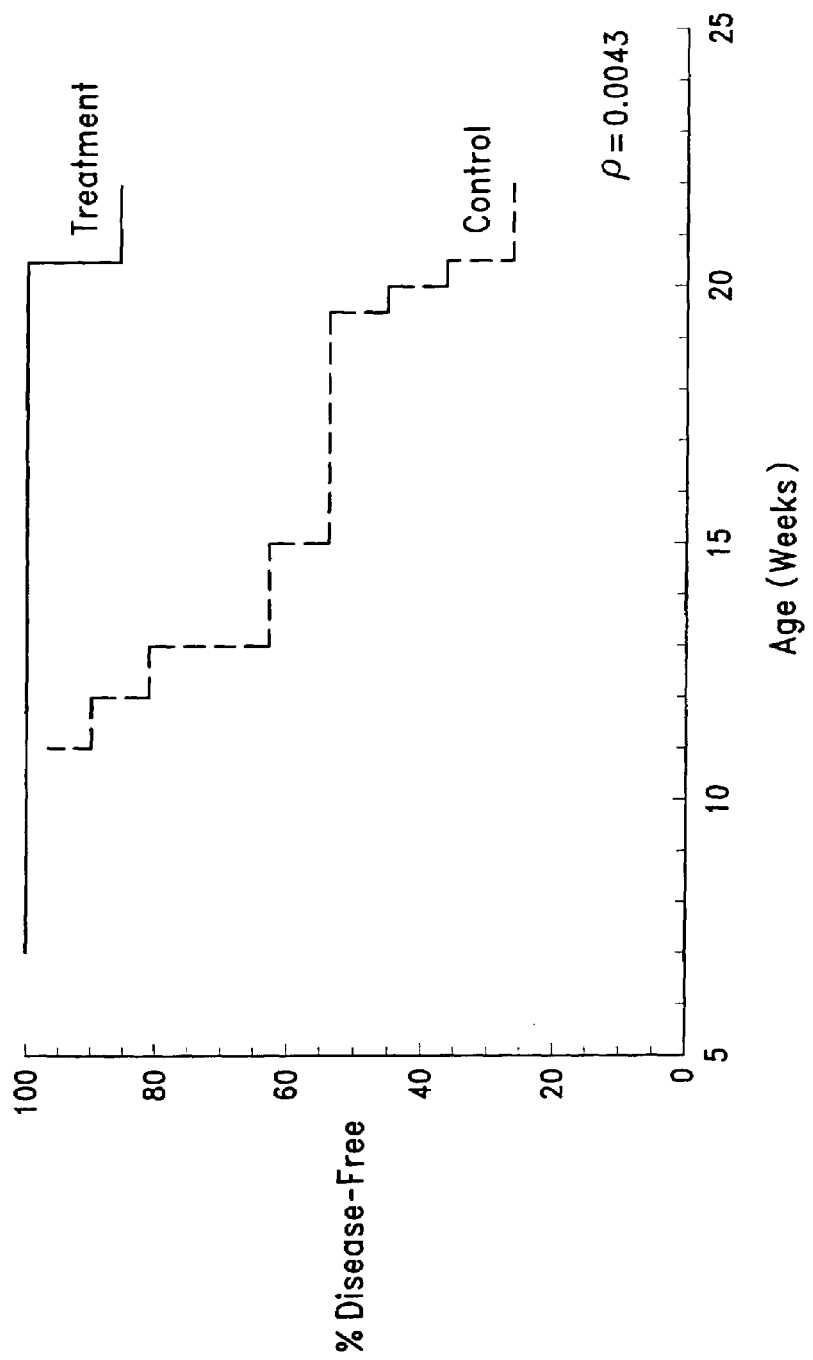
FIG. 3 depicts disease progression analysis for MRL-lpr mice treated according to the methods described herein (solid line) as compared to controls (dotted line). The percentage of disease-free animals (y-axis) is plotted over time (x-axis).

FIG. 3 provides disease progression analysis for mice treated 60 mg/kg qod. Similar data are obtained with the 30 mg/kg qod dosing schedule. As seen in FIG. 3, treating mice with Compound 1 significantly delays the onset of and effectively treats the lupus-like disease relative to the control mice (p=0.0043). These data are supported by the observation that BUN values for the treated animals are normal whereas those receiving vehicle alone are in renal distress.

Laboratory Diagnostics

The blood from the animals was analyzed for alterations in total numbers of white blood cells (WBC) as well as differential representation of subtypes. Mice receiving Compound 1 (60 mg/kg) have nearly identical values for hematocrit, platelet count, and WBC relative to those receiving vehicle alone (Table 2).

HCT, hematocrit (%); PLAT, platelets (K/µL); WBC, white blood cells (K/µL); POLYS, polymorphonuclear cells (%); LYMPHS, lymphocytes (%); MONO, monocytes (%); EOS, eosinophils (%); BASO, basophils (%).

Autoantibodies

Serum samples from all of the mice were analyzed to determine the titer of antibodies to several autoantigens (Table 3). These antibodies are total serum polyclonal antibodies. At the termination of the study, the mice receiving Compound 1 showed significantly lower titers of antibodies to ssDNA (p=0.019), histones (p=0.0056), and La antigen (p=0.0265). Anti-dsDNA titers were lower in the treatment mice but not statistically different from those in the control animals (p=0.082). There was also no difference in antibodies to Ro antigen between the two groups of mice; however, the actual absorbance measurements were very low for these ELISAs and any differences may have been masked by the sensitivity of the assay. Anti-Sm titers were only observed in a few of the animals in both groups and no conclusions could be made regarding differences between the groups. These anti-Sm findings are consistent with the literature, which reports that only 10% of MRL-lpr mice are expected to be positive for antibodies against Sm antigen (Murphy, E. D. (1981). For data on lymphoproliferation (lpr) and other single-locus models for murine lupus, see *Immunologic Defects in Laboratory Animals* (E. M. Gershwin and B. Merchant, eds.); Vol. 2, pp. 143–173 (Plenum, N.Y.). The observed differences in autoantibody levels are found in a background of very high total IgG concentrations which do not differ statistically between the control and the treatment groups (p=0.3312).

TABLE 2

Complete Blood Count with Differential (mean ± standard deviation).

| Group | HCT | PLAT | WBC | POLYS | LYMPHS | MONO | EOS | BASO |
| --- | --- | --- | --- | --- | --- | --- | --- | --- |
| Control | 46.70 | 809 | 13.22 | 31.50 | 65.07 | 2.35 | 0.88 | 0.13 |
|  | (0.91) | (129) | (4.65) | (8.38) | (9.61) | (2.03) | (0.42) | (0.06) |
| Treatment | 42.60 | 895 | 13.68 | 43.00 | 53.66 | 2.01 | 1.15 | 0.17 |
|  | (7.57) | (148) | (7.27) | (16.37) | (16.81) | (1.05) | (1.95) | (0.27) |
| p value | 0.267 | 0.183 | 0.5 | 0.069 | 0.069 | 0.473 | 0.147 | 0.267 |

TABLE 3

Autoantibody Titers

|  | Anti-ssDNA (U/ml) | Anti-dsDNA (U/ml) | Anti-Histone* (OD) | Total IgG (mg/ml) | Anti-Ro (U/ml) | Anti-La (U/ml) |
| --- | --- | --- | --- | --- | --- | --- |
| Drug Group | 508 ± 193 | 247 ± 101 | 0.613 ± 0.526 | 23.3 ± 6.2 | 304 ± 256 | 226 ± 162 |
| Control Group | 887 ± 328 | 650 ± 454 | 1.387 ± 0.537 | 25.8 ± 8.7 | 456 ± 328 | 529 ± 462 |
| p value | 0.019 | 0.082 | 0.0056 | 0.3312 | 0.1588 | 0.0265 |

*Titers were not available at the time of this report. Anti-histone levels are reported as $OD_{405}$ values at a 1/400 dilution of serum.

Joint Histology

In addition to the lupus syndrome, MRL-lpr mice spontaneously develop an erosive arthropathy that resembles human rheumatoid arthritis, both histologically and serologically. The arthritic lesions in these mice are characterized by inflammatory changes in the synovium and the periarticular connective tissue, frequently accompanied by the presence of circulating rheumatoid factors in the serum. This arthritic process is progressive and proceeds through several different stages from a mild synovitis to an erosive arthritis, which can eventually lead to a scarred joint. Histologically, the majority of 5 month old MRL-lpr mice demonstrate synovial cell proliferation, destruction of articular cartilage and subchondral bone, infiltration of synovial stroma by inflammatory cells, periarticular inflammation (vasculitis, myositis, tendinitis, perineuritis), exudates, pannus formation, and subcutaneous fibrinoid nodules (Hang, L. et al. (1982) *J. Exp. Med.* 155:1690–1701; Koopman, W. J. and Gay, S. (1988) *Scand. J. Rheumatology. Suppl.* 75:284–289).

The paws of all the mice treated with Compound 1 were examined for signs of arthritis and synovitis. The control mice (those receiving vehicle alone) have a severe synovitis characterized by a marked thickening of the synovium with occasional formation of papillary, villous configurations. Typically, the synovial pathology was a result of synovial cell proliferation and infiltration of the synovial stroma by inflammatory cells. In a substantial percentage of the control mice, the disease process was accompanied by pannus formation and erosion of the articular surface (both articular cartilage and subchondral bone). In contrast, the treatment mice were found to have a milder synovitis as well as fewer erosions and limited pannus formation (Table 4). The character of the disease in the animals receiving Compound 1 was much less aggressive with less synovial cell proliferation and inflammatory infiltration. Of further interest, it was observed that the treatment mice had a lessened degree of periarticular inflammation. The combination of these findings suggest that Compound 1 is ameliorating the arthritic disease process that typically destroys the joints of MPL-lpr mice.

TABLE 4

Synovial Pathology

| Group | Number of mice | Average Histologic Score Synovitis | Number of Mice with Synovitis ≧ 2† | Number of Mice with Erosions† | Number of Mice with Pannus Formation† |
|---|---|---|---|---|---|
| Control | 7 | 2.1 | 5 (71%) | 4 (57%) | 4 (57%) |
| Treatment | 7 | 1.3 | 0 (0%) | 1 (14%) | 1 (14%) |
| p value | | p = 0.001 | p = 0.01 | p = 0.13 | p = 0.13 |

†p value determined by cross-tabulation and chi-square analysis.

Delayed Type Hypersensitivity (DTH)

Figure 4A:
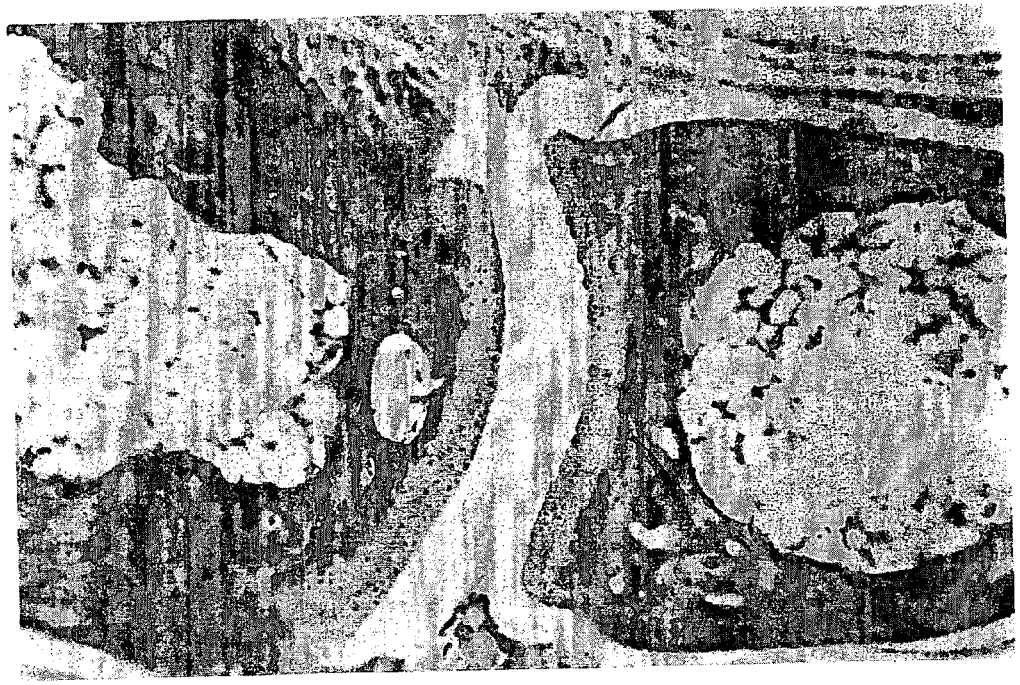
FIGS. 4A–4C depict footpad swelling in MRL-lpr mice treated according to the methods described herein (FIG. 4A) as compared to controls (FIG. 4B).
Figure 4B:
Figure 4C:
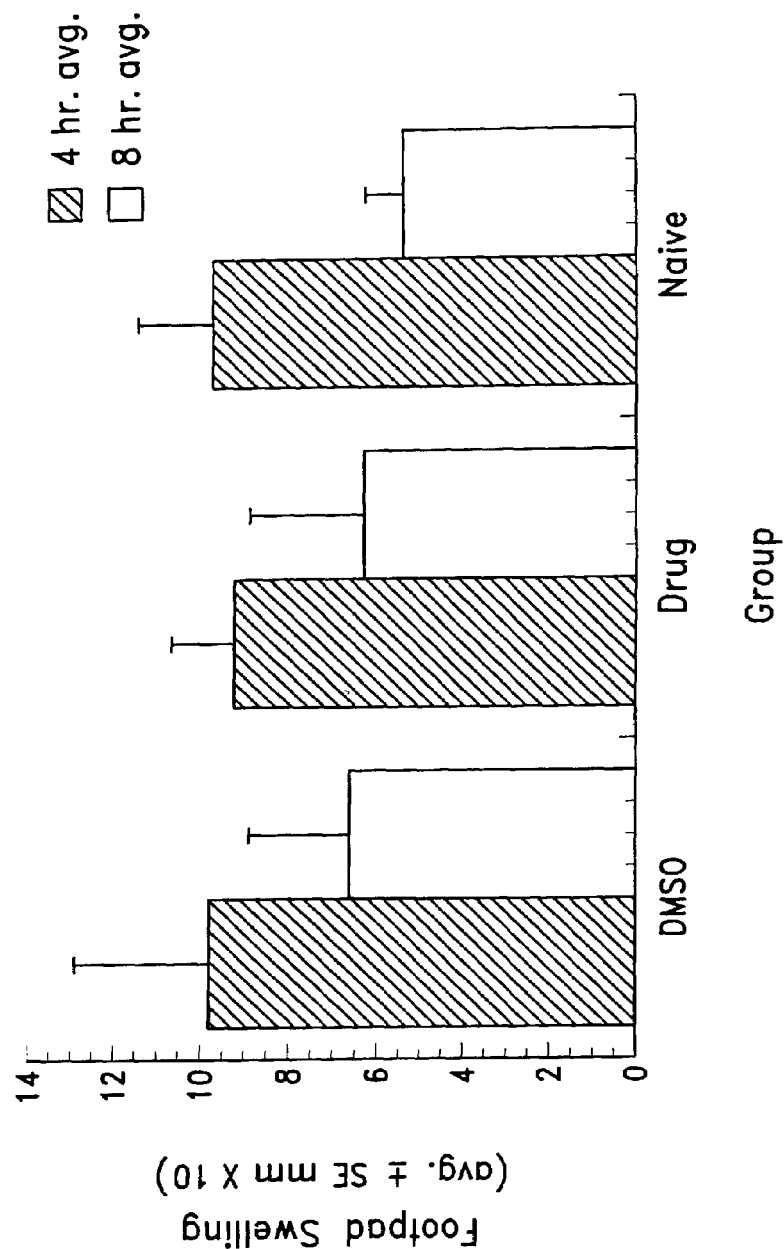
Figure 5:
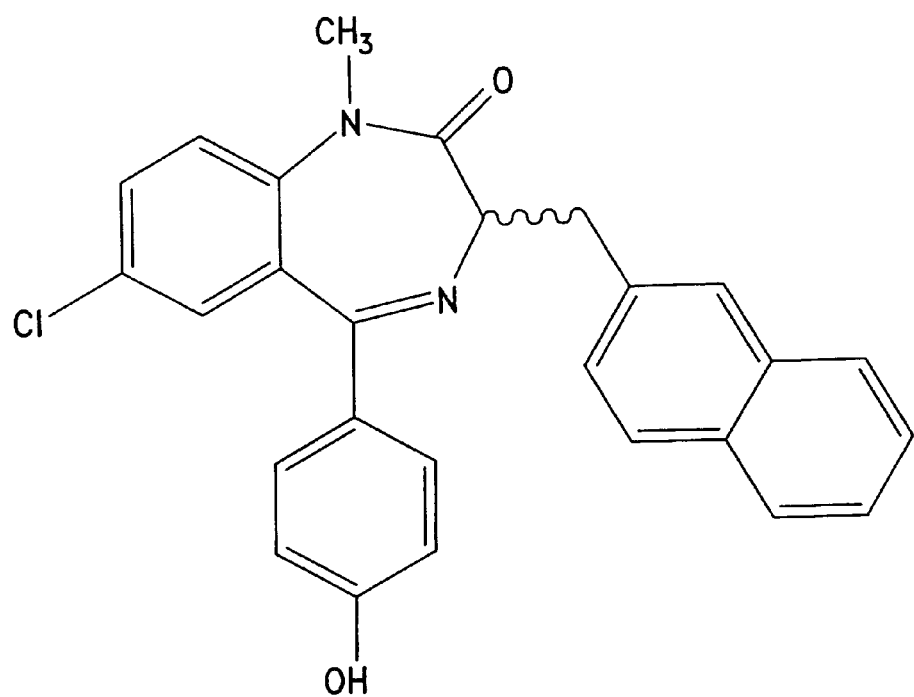
FIG. 5 shows the structure of Compound 1 (Bz-423).

Mice treated with Compound 1 (60 mg/kg) showed no difference in DTH response to TNBS on comparison to the control mice (FIG. 4C). Importantly, neither group of animals demonstrated a significant footpad swelling following antigen challenge. This phenomenon has been documented and old MRL-lpr mice (>10 weeks) are expected to have a diminished in vivo T cell response to stimulus as evidenced by the absence of a DTH response. See Okuyarna, H. et al. (1986) *Clin. Exp. Immunol.* 63:87–94, and Scott, C. F. et al. (1984) *J. Immunol.* 132:633–639. However, suppression of T cells can result in a rescue of the DTH response. See, Okuyama, H. et al. (1989) *Int. Arch. Allergy Appl. Immunol.* 1588:394–401. Such a rescue was not observed in this study's treatment protocol. These data suggest that Compound 1 does not alter T cell function. FIGS. 4A–4C show the results of the Footpad Swelling experiment.

Immune Cell Function

Thymidine uptake assays of using both stimulated and unstimulated T and B cells was conducted to determine if Compound 1 affects lymphoproliferation in vitro. At about a concentration of 10 µM, no effect on lymphocyte proliferation was observed.

Example 3

Compound 1 as a Lymphotoxic Agent

Methods

Animals and experimental design: Female NZB/W mice (Jackson Labs) were housed in specific pathogen-free, environmentally controlled rooms operated by the University of Michigan's Unit for Laboratory Animal Medicine with 12 hr light-dark cycles and were given food and water ad libitum. Mice were randomly distributed into treatment and control groups. All mice were dosed through intraperitoneal injections using a Hamilton repeating dispenser with glass microliter syringes and 30 gauge needles. Control mice received vehicle (50 µL aqueous DMSO) and treatment mice received Compound 1 dissolved in vehicle. Animal weights were determined weekly, and dosing schedules readjusted thereafter.

Collection of Blood/Tissues: Peripheral blood was obtained from the tail veins of all mice for complete blood counts analysis and collection of serum. Blood was first allowed to clot at room temperature for 1 h, and then overnight at 4° C. Serum was separated from the formed clot by centrifugation (6 min., 16,000×g). A section of spleen was removed aseptically for preparation of single cell suspensions. Samples of the following organs were preserved in 10% buffered-formalin: heart, liver, lung, spleen, kidney small intestine, reproductive system, salivary glands, thymus, mesenteric and axillary lymph nodes, and skin. Additional sections of kidney and spleen were preserved by snap-freezing in OCT. Bone marrow smears were prepared from each femur.

Histology: All histological determinations were made in a blinded fashion by a pathologist. Formalin-fixed sections were cut and stained with hematoxylin and eosin (H&E) using standard protocols (Luna, L. G., in: Manual of Histological Staining Methods of the Armed Forces Institute of Pathology, McGraw-Hill, New York (1960)). Immune-complex deposition in the kidneys was evaluated by direct immunofluorescence using frozen sections stained with FITC-conjugated goat anti-mouse IgG (Southern Biotechnology Associates, Birmingham, Ala.) and C3 (Cappel-Organon Teknika, Durham, N.C.). The degree of lymphoid hyperplasia was scored 0–4+ scale.

TUNEL staining: Frozen spleen sections (4 pm thick) were assayed for DNA strand breaks using the In Situ Cell Death Detection kit (Roche Molecular Biochemicals) according to the manufacturer's protocols. Sections were analyzed using a 0–4+ scale. Sections were blindly evaluated and assigned a score on the basis of the amount of TUNEL-positive staining.

Fluorescence analysis of lymphocyte populations: Single cell suspensions were prepared by teasing apart the spleen in media, followed by removal red blood cell with isotonic lysis buffer (Kruisbeek, A. M., in: Current Protocols in Immunology, eds., Coligan, J. E. et al., pp. 3.1.2–3.1.5, John Wiley & Sons, Inc. (1997)). 10⁶ cells were stained at 4° C. with fluorescently-conjugated anti-Thy 1.2 (Pharmingen, clone: 53-2.1, 1, μg/mL) and/or anti-B220 (Pharmingen, clone: RA3-6B2 1, μg/mL) for 15 min. In samples stained to detect outer-membrane phosphatidyl serine, cells were then incubated with FITC-conjugated Annexin V and PI according to manufacturer protocols (Roche Molecular Biochemicals). Cells were analyzed on a Coulter ELITE flow cytometer. For each sample, at least 10,000 events were counted.

Serum Anti-DNA: Titers were determined by direct ELISA as previously described (Swanson, P. C. et al., *J. Clin. Invest.* 97:1748–1760 (1996)). Detection of IgG anti-DNA used an alkaline phosphatase-conjugated Goat anti-Mouse IgG (H-chain only) secondary antibody (1/1000 dilution, SIGMA). To convert absorbance readings into titers, pooled serum from unmanipulated eight month old female NZB/W was used as a reference standard which was arbitrarily assigned a value of 1000 U/mL.

Serum Immunoglobulin: Concentrations were determined by capture ELISA. Goat anti-Mouse Ig (Southern Biotechnology Associates) was diluted to 10 pg/mL in PBS and coated overnight at 4° C. on Immulon II microtiter plates. Otherwise, ELISAs were performed as previously described. To convert absorbances into concentrations, a standard curve was generated using a previously quantified mouse immunoglobulin reference serum (ICN Biomedicals, Aurora, Ohio).

Blood urea nitrogen (BUN) and complete blood counts (CBC): Serum BUN measurements were conducted by the University of Michigan Hospital's clinical pathology laboratory. CBC analyses were conducted by the diagnostic laboratory of University of Michigan's Unit for Laboratory Animal Medicine. Automated counts determined by a Hemavet 15 OR were confirmed by visual examination of blood smears.

Serum 1,4-benzodiazepine levels: Serum samples from mice injected with Compound 1 were precipitated with acetone (5× volume, −20° C., 10 min). After centrifugation (16000×g, 10 min), the supernatant containing Compound 1 was concentrated in vacuo, and then extracted from any remaining protein using a Sep-pak C18 column (Waters Corp.) running a step gradient from 10% acetonitrile in water to 100% acetonitrile. Material eluting in the organic fraction was concentrated in vacuo, and then analyzed by reversed-phase HPLC using a Phenomenex C18 column. Peak areas were determined using a Shimadzu integrator and were referenced to a standard curve.

Statistical Analysis: Statistical analyses was conducted using the SPSS software package. The Mann-Whitney U and chi-square tests were used for histological and clinical data. Student's t-test was used for flow cytometric data. Correlations were assessed by ANOVA.

Example 4

Figure 6A:
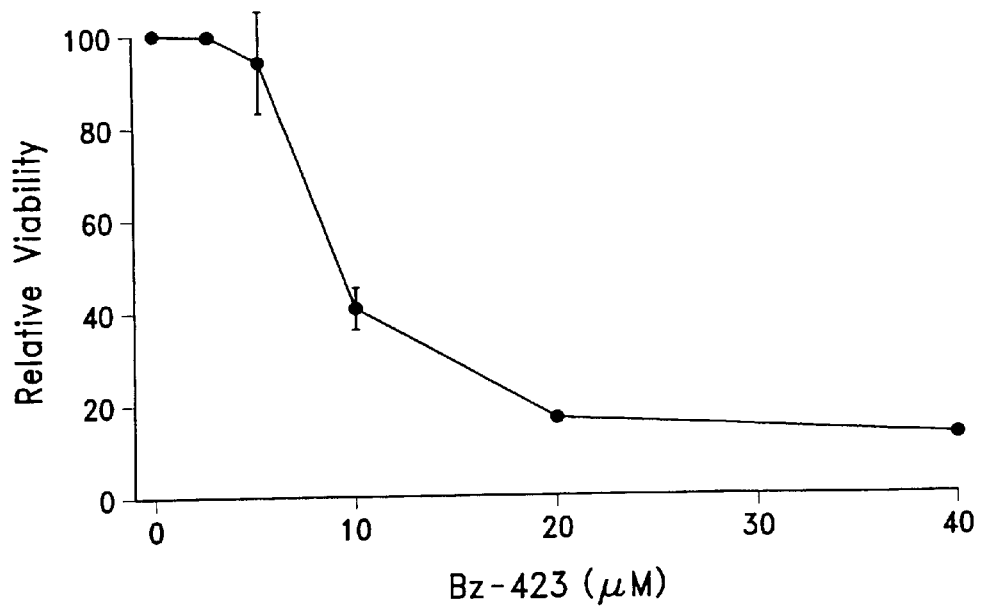
FIGS. 6A–6B are graphs depicting the in vitro treatment of NZB/W C splenocytes.
Figure 6B:
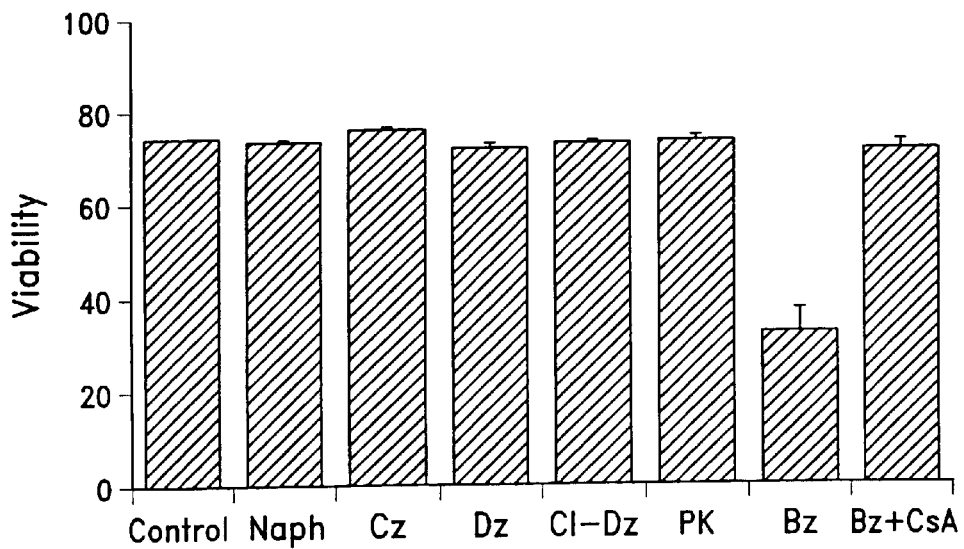

A series of experiments were conducted to characterize the nature of cell death caused by Compound 1 in terms that could point toward the death mechanism. Compound 1 treated cells stained positive in TUNEL assays suggesting treatment resulted in free-ends of DNA (Gorczyca, W. et al., *Leukemia* 7:659–670 (1993)), a feature of apoptosis. Caspase activity and mitochondrial permeability are two central components of the intracellular death machinery (See, Zamzami, N. et al., *J. Exp. Med.* 183:1533–1544 (1996) and Los, M. et al., *Immunity* 10:629–639 (1999)). Cyclosporin A (CsA) regulates the mitochondrial permeability transition (MPT) (Zoratti, M. and Szabo, I., *Biochim. Biophys. Acta* 1241:139–176 (1995)), protecting cells from death pathways that rely on the release of apoptogenic factors from the mitochondria. CsA provided dramatic protection against Compound 1, such that 90% of the cells that would have been killed by Compound 1 survive when CsA (10 μM) is added to the culture (FIG. 6B). Pretreating cells with z-VAD-fmk (20 pM), a non-specific caspase inhibitor (Garcia-Calvo, M. et al., *J. Biol. Chem.* 273:32608–32613 (1998)), protects cells to a lesser extent: viability in z-VAD-fmk pretreated cells is 25% greater than cells treated with Compound 1 alone. Together, these data suggest that Compound 1-induced death of NZB/W lymphocytes requires the MPT while caspase activation is of secondary importance.

To determine if the effects on lymphocytes in vitro also occur in vivo, 8-month old female NZB/W mice were dosed with Compound 1 (60 mg/kg IP daily). This dose results in peak serum concentrations of 10 μM (1 h post-injection) with trough levels of 1–2 μM (18–24 h post-injection). After 7 days, mice were sacrificed and their spleen cells examined by flow cytometry. Splenocyte viability, measured on the basis of PI exclusion, was significantly decreased in treated versus control injected animals as shown in Table 5, below.

TABLE 5

|  | Cell Viability (PI⁻) | Apoptotic B-cells (B220⁺, Thy1.2⁻) | Apoptotic T-cells (B220⁻, Thy1.2⁺) |
|---|---|---|---|
| Control | 85 ± 2 | 25 ± 5 | 12 ± 4 |
| Bz-423 | 81 ± 2 | 32 ± 6 | 12 ± 9 |
|  | p = 0.003 | p = 0.02 | p = 0.50 |

Flow cytometric measurements of splenocytes after in vivo treatment.

In this experiment, 8 month old NZB/W mice were divided into treatment and control groups of seven mice each. Treatment mice were dosed with Compound 1 (60 m kg qd) and the controls received vehicle (50 μL DMSO qd) for 7 days. The overall viability of the splenocytes isolated from each mouse was determined on the basis of PI exclusion. The decrease in viability is smaller than that observed after in vitro treatment because intervening processes (i.e., cell recruitment, proliferation and clearance of early apoptotic cells by the reticuloendothelial system (RES)) decrease detectable splenocyte death. Apoptotic cells are shown as a percentage of PI-excluding B- and T-cells. Mixed splenocytes were isolated from treated animals and then placed in culture briefly (2×10⁶ cells/mL for 3 h in RPMI containing 10% FBS) to allow expression of the apoptotic phenotype in the absence of RES clearance. Subsequently, cells were stained with Annexin V-FITC, PI and monoclonal antibodies specific for either Thy-1.2 or B 20. Each value is based on the flow cytometric analysis of 20,000 viable cells.

Treatment of NZB/W Mice with Compound 1

At therapeutic doses, current treatments for organ-threatening lupus severely deplete all lymphoid cells, resulting in serious side effects associated with immunosuppression (Donadio, J. V. and Glassock, R. J., *Am. J. Kidney Dis.* 21:239–250 (1993)). The B cell selectivity coupled with the moderate overall effect on splenic lymphocyte viability distinguish Compound 1 from these treatments. Hence, Compound 1 represents a lead compound in a new class of lymphotoxic agents possibly with a favorable benefit-toxicity profile. To determine the effect of Compound 1 on autoimmune nephritis and how long-term dosing affects the immune system, a longitudinal treatment study was conducted using female NZB/W mice.

In this study, mice received intraperitoneal injections of Compound 1 (n=25; 60 mg/kg), or vehicle (n=20) every other day over 3 mo. from 6.5 to 9.5 mo. of age. This time span represents a point after the onset of glomerulonephritis and continues through the 50% mortality point (Theofilopoulos, A. N. and Dixon, F. J., *Adv. Immunol.* 37:269–390 (1985)). Mice were sacrificed periodically and examined for the impact of Compound 1 on nephritis and the peripheral immune system.

Figure 7:
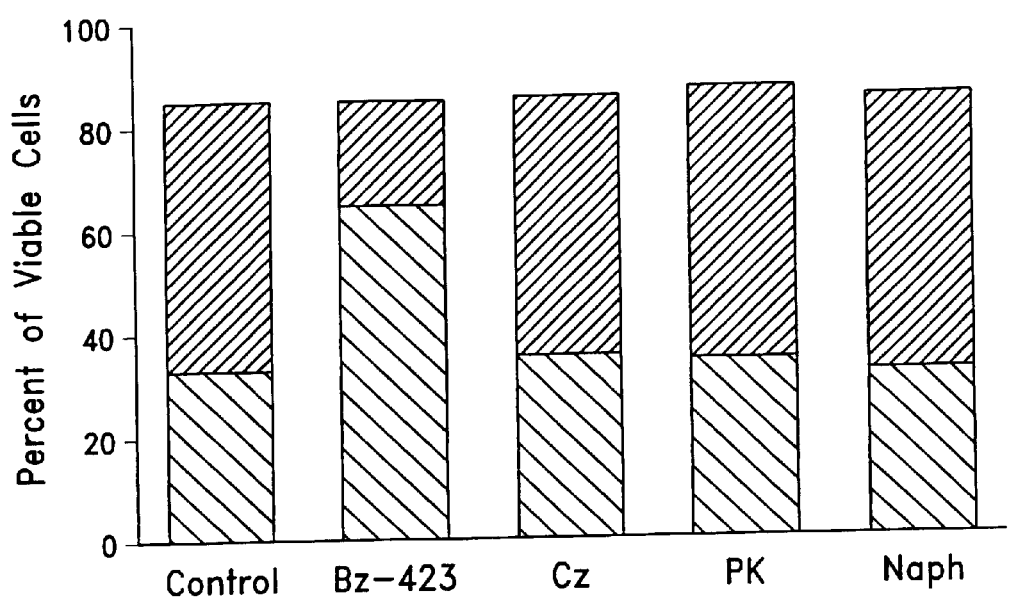
FIG. 7 depicts the in vitro analysis of cell populations. Experimental conditions are identical to FIG. 6. Solid bars represent the percentage of viable cells staining with B220 (B-cells) after treatment with the indicated agent. Hatched bars represent cells staining with Thy1.2 (T-cells).
Figure 8:
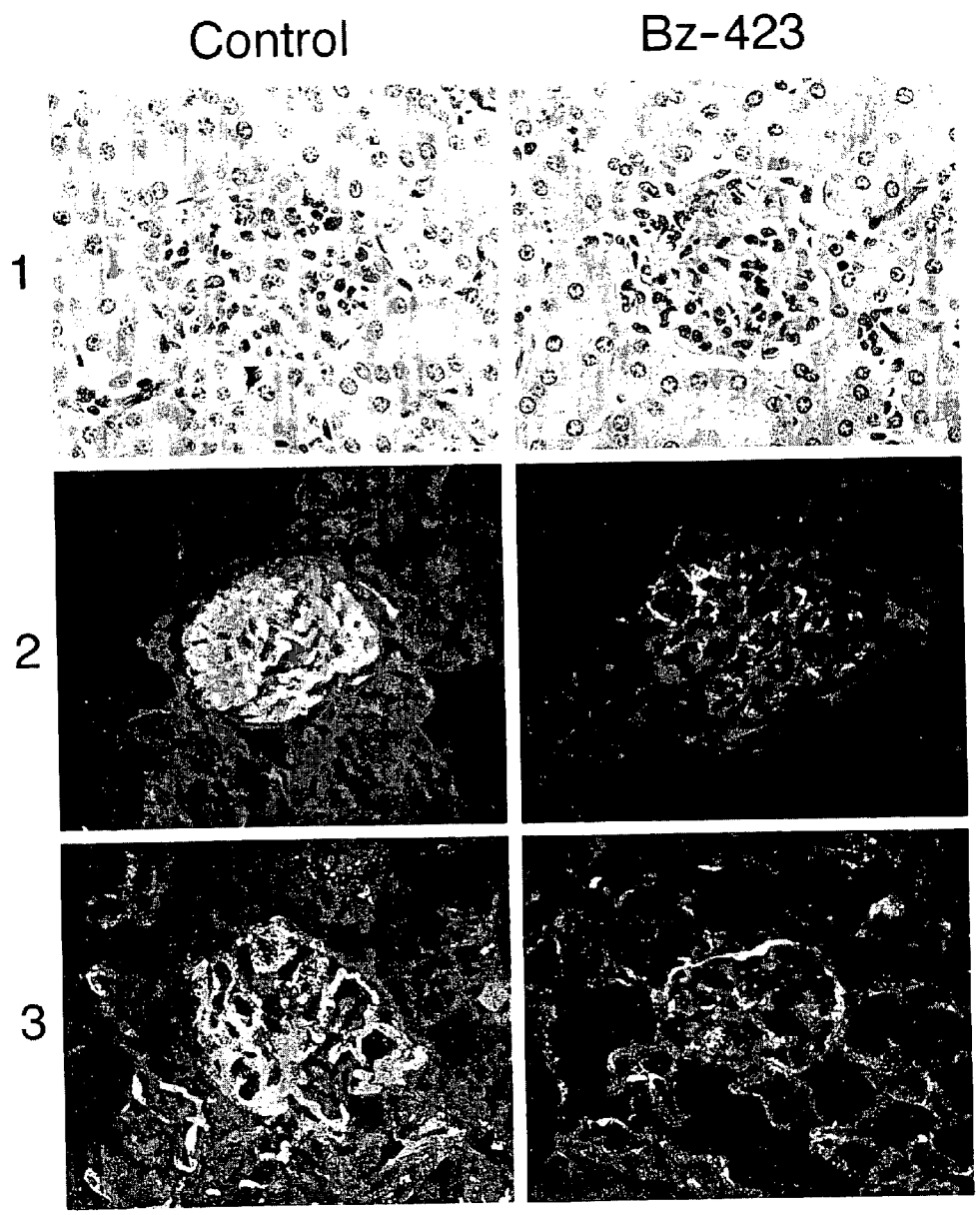
FIG. 8 is a series of photographs showing representative glomeruli from NZB/W mice. Panel 1—H&E, panel 2—IgG deposition, and panel 3—complement C3 deposition. All sections were photographed at 400×.
Figure 9:
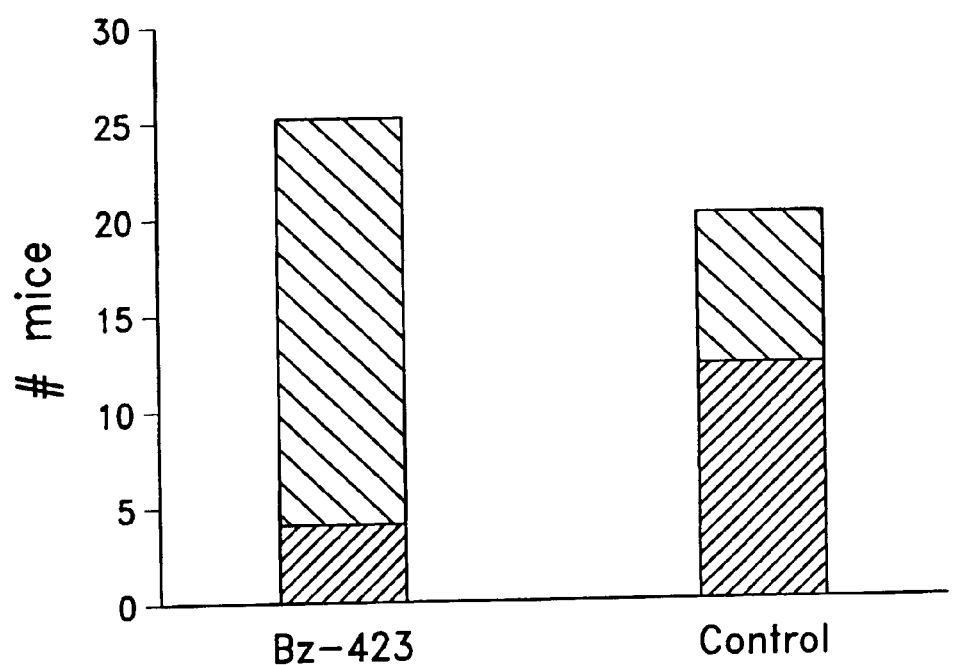
FIG. 9 shows that treatment with Compound 1 prevents the development of autoimmune glomerulonephritis. H&E stained kidney sections were analyzed for degree of nephritis using a 0–4+scale. Solid bars represent mice with disease (>2+) at time of sacrifice, while hatched bars represent healthy mice (<2+); p<0.003.

Microscopic examination of kidney tissue reveals that treatment with Compound 1 is protective throughout the course of treatment. Kidney sections taken from control mice indicate a diffuse, proliferative glomerulonephritis with proliferation of all cellular elements and occasional wire-loop formation consistent with an average histopathologic score of 3+ (FIGS. 6 and 7). In contrast, treatment mice have much milder changes with less cellular proliferation and wire-loop formation and a score of 1+($p<0.002$). As seen in FIG. 6, administration of Compound 1 reduced both glomerular IgG and C3 deposition throughout the course of treatment (IgG, $p<0.003$; C3, $p<0.04$). The degree of deposition within an individual mouse strongly correlates with its histopathologic score: mice with reduced Ig deposition show less glomerular injury ($p<0.002$). Mechanistically, this finding is consistent with lymphoid cell death in vivo, presumably leading to fewer (pathogenic) B cells.

The histological differences observed between the treatment and control groups were confirmed by clinical measures of kidney function. At the time of sacrifice, 85% of control mice have abnormally high blood urea nitrogen (BUN) levels (2 30 mg/dL) (Gordon, C. et al., *Clin. Immunol. Immunopath.* 52:421–434 (1989)), while 31% of treatment mice have elevated BUN ($p<0.007$). Similarly, 39% of control mice have significant proteinuria (>100 mg/dL) (Adelman, N. E. et al., *J. Exp. Med.* 158:1350–1355 (1983)), while only 18% treatment mice developed this finding ($p<0.11$). For each mouse, the histological score is strongly correlated with both the proteinuria and BUN levels ($p<0.002$); the mice with less severe disease have lower proteinuria and BUN titers. These data confirm that the histological measures of nephritis reflect the functional status of the kidneys. Together, these findings indicate that Compound 1 protects NZB/W mice from both the progression and the effects of autoimmune glomerulonephritis.

Compound 1 Reduces B Cell Number

Figure 10:
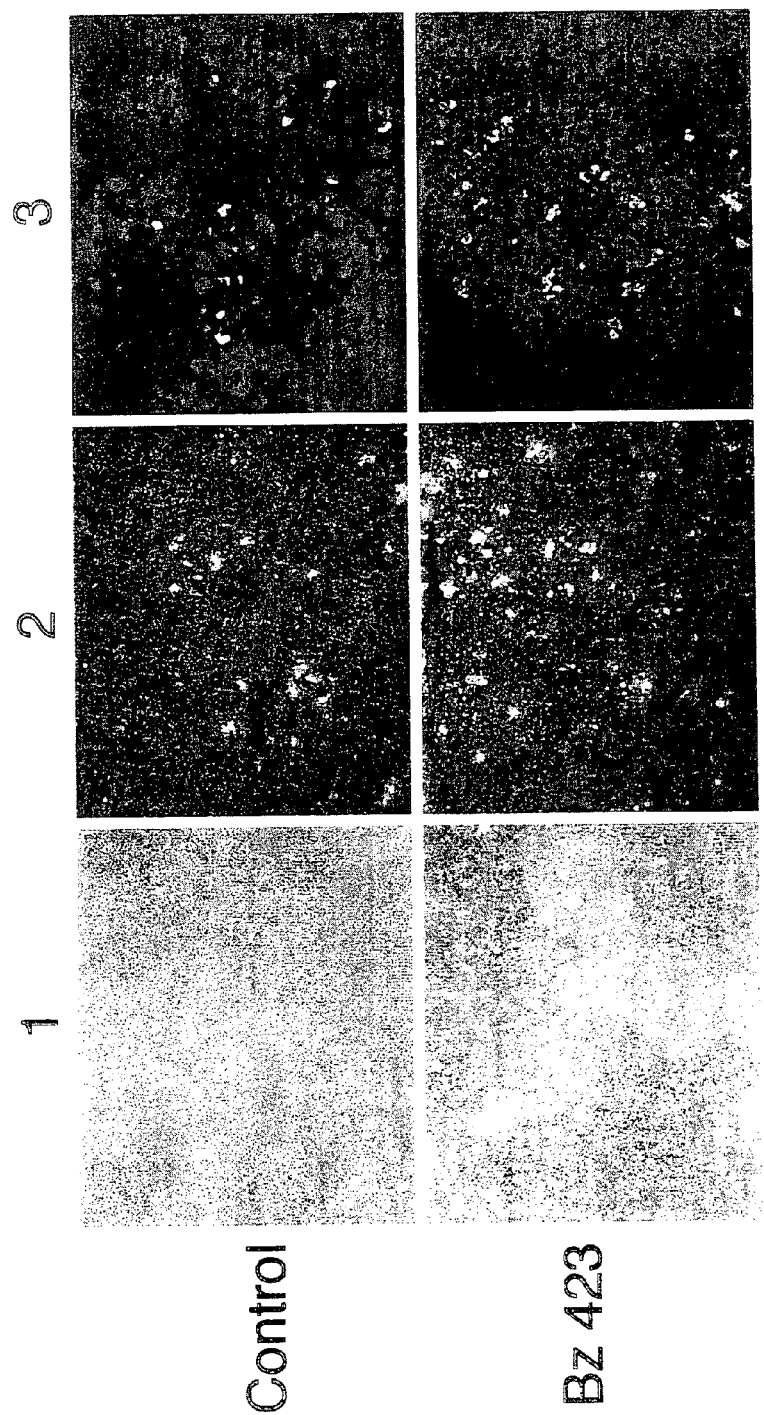
FIG. 10 is a photograph of representative spleen sections from NZB/W mice. Panel 1—low power (50×) H&E sections indicating a decrease in lymphoid content in treatment mice. Panel 2—medium power (200×) sections indicating increased numbers and clustering of TUNEL positive-cells in the treatment mice. Panel 3—high power (400×) sections co-stained for TUNEL-positive cells (green) and B220 (red) indicating increased numbers of B220$^+$ TUNEL positive cells in the treatment mice.

NZB/W mice develop disease-related lymphoid hyperplasia marked by an expansion of B-cells that coincides with the increase in serum autoantibody titers (See, Theofilopoulos, A. N. and Dixon, F. J., *Adv. Immunol.* 37:269–390 (1985) and Ermak, T. H. et al., *Lab. Invest.* 61:447–456 (1989)). Spleens from control mice reflect this phenomenon: an expansion of the white pulp is observed causing both distortion of normal spleen architecture and a reduction in the red pulp (FIG. 10). The mice that received Compound 1 have a more normal balance of red and white pulp. Scoring multiple spleen sections from all treatment and control animals revealed a statistically significant reduction of lymphoid hyperplasia in the treatment group (2+vs. 3+ on a 0–4+ scale; $p<0.02$).

The constitution of the splenic lymphoid cell compartment after 6 and 12 wk of treatment was analyzed by flow cytometry. As shown in Table 6, Compound 1 reduces the B cell fraction by 10–15% relative to control mice ($p<0.05$), whereas the fraction of T-cells remains unaffected by treatment.

TABLE 6

| Timepoint | Control | B cells (B220$^-$Thy1.2$^-$) | T-cells (B220$^+$Thy1.2$^+$) |
|---|---|---|---|
| 6 week | Control | 58 ± 5 | 18 ± 6 |
| | Bz-423 | 49 ± 5 | 26 ± 5 |
| | | p = 0.04 | p = 0.10 |
| 12 week | Control | 67 ± 5 | 17 ± 5 |
| | Bz-423 | 59 ± 6 | 16 ± 4 |
| | | p = 0.04 | p = 0.40 |

Flow cytometric determination of splenic lymphocyte populations present after longitudinal treatment.

This difference can be explained either by an effect on lymphocyte proliferation or by the selective reduction of lymphocytes. Since Compound 1 does not alter splenocyte proliferation in vitro, we favor the later explanation. That no significant increase in the fraction of T cells is observed, suggests killing of T cells occurs to a lesser extent than killing of B cells, which is consistent with the findings from the in vitro studies and short term dosing experiments presented above.

To directly determine the effect of Compound 1 on lymphoid cell death in vivo, splenic tissue was analyzed for evidence of cell death using the TUNEL reaction. In sections from 10 representative control mice, TUNEL-positive cells amount to less than 1% of the total number of cells and the staining was randomly dispersed throughout the section. By contrast, mice treated with Compound 1 possess up to a 5-fold increase in numbers of TUNEL-positive cells (ca. 3+ staining) in 50% of the sections ($p<0.05$). Unlike the sections from the control mice, the TUNEL-positive cells in these sections show prominent clustering (FIG. 10). Combined TUNEL analysis and immunohistochemical staining for a B-cell surface marker (B220) indicate that cells demonstrating drug-induced TUNEL positivity are B-cells (FIG. 10).

The action of Compound 1 against B cells and the improvement in autoantibody-mediated renal disease predicts a decrease in autoantibody titers. Serum obtained during the course of treatment was assayed for total IgG as well as anti-dsDNA. Total immunoglobulin levels are not altered over the course of treatment (e.g., after 9 weeks of treatment, control=4.0±2.2 mg/mL; Compound 1=4.0+1.3 mg/mL, $p>0.4$). In contrast, anti-dsDNA titers are reduced after 3 weeks of treatment with Compound 1 (control=733+546 U/mL; Compound 1=496+513 U/mL, $p<0.06$). However, by about 9 weeks of treatment anti-dsDNA levels in treated mice are indistinguishable from controls (control=812+695 U/mL; Compound 1=944+546 U/mL, $p>0.3$). The early drop in anti-dsDNA in the context of unchanged total IgG coupled with the observation that glomerular Ig deposition is reduced throughout the entire course of treatment, suggests that pathogenic cells may have a enhanced sensitivity to Compound 1.

Given the progressive nature of the disease in NZB/W mice, it is likely that the eventual rise of anti-dsDNA corresponds to a point characterized by increased B-cell proliferation, for example, as can bee seen in Table 6. This hypothesis is also supported by the observation that administering twice the dose of compound results in a sustained reduction of anti-dsDNA with disease improvement roughly equivalent to that seen with the lower dosing.

In summary, these observations link treatment with Compound 1 to disease improvement, as reflected by renal histology, renal function, autoantibody, and C3 deposition, and provides evidence that this therapeutic effect coincides with the ability of the compound to selectively induce cell death in B-cells.

Compound 1 is not Toxic

Animal tissues were examined for evidence of toxicities commonly associated with cytotoxic drugs. Compound 1 does not affect gross animal weight and mice receiving Compound 1 do not have altered grooming practices or noticeably different behaviors. Microscopic examination of the heart, liver, lung, salivary glands, small intestine, and uterus demonstrated no significant architectural differences between control and treatment groups. Further comparing the control and treatment groups revealed that Compound 1 did not increase the number of apoptotic cells in the non-lymphoid organs. No evidence of increased pneumonitis was seen in the lungs of the treated animals which is an important indicator of serious infection commonly observed in animal studies using cytotoxic drugs (Horowitz, R. E. et al., Lab. Invest. 21:199–206 (1969) and Hahn, B. H. et al., Arthritis Rheum. 18:145–152 (1975)). The lack of excess pneumonitis in treated animals is strong evidence against a significant immunosuppressive effect. Examination of bone marrow smears revealed no differences between treatment and control animals with respect to overall cellularity or in the proportional representation of specific myeloid and erythroid precursors. Peripheral blood counts and differential white blood cell analysis revealed no decreases in platelets, granulocytes, lymphocytes, or hematocrit. In aggregate, no evidence of generalized immune suppression or other toxicities were detected in mice treated with Compound 1.

Example 5

To model neuroblastoma in mice, the mice were transfected with the human neuroblastoma cell line SKNAS, to cause the cells to overexpress the neuroblastoma associated human oncogene N-myc. The resulting cell line is designated as D2. These cells form tumors when xenografted into T cell-deficient athymic mice; thus providing a relevant animal model of human neuroblastoma.

Figure 11:
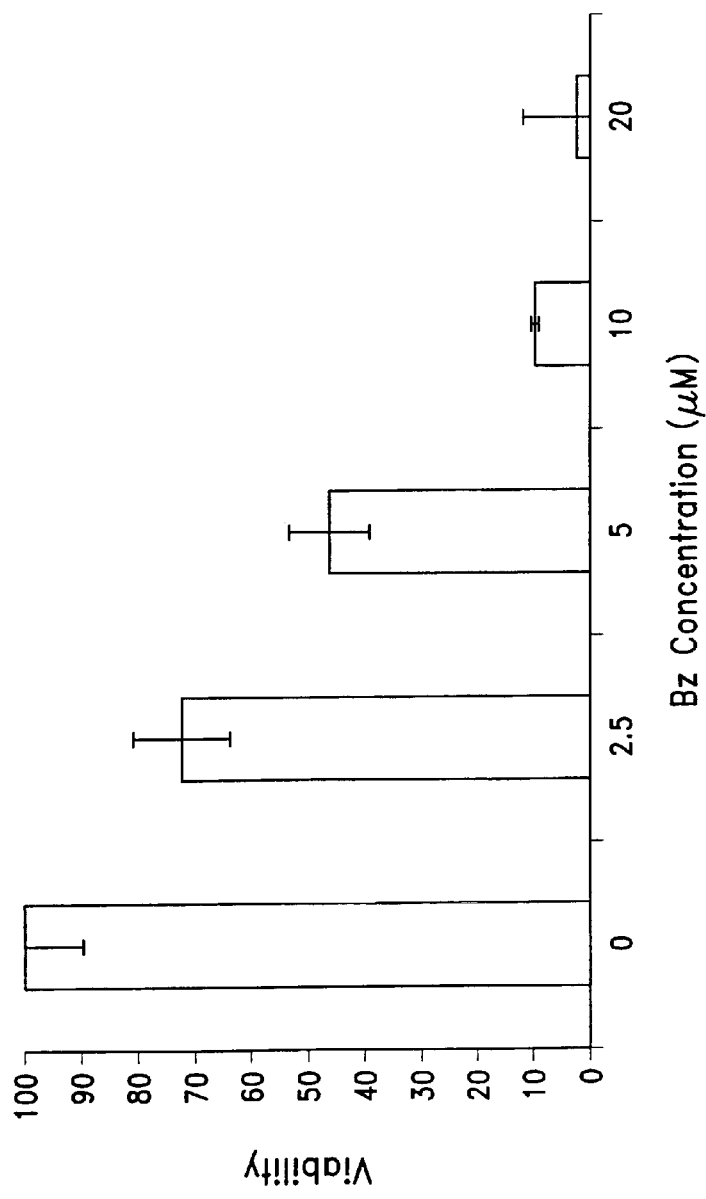
FIG. 11 is a bar graph depicting the efficacy of using benzodiazepine to kill D2 neuroblastoma cells in vitro

In vitro testing of the D2 cells was conducted to determine their sensitivity to benzodiazepine. D2 cells were plated into 96-well tissue culture plates at a density of 10,000 cells per well in culture media (DMEM, 10% V:V heat inactivated fetal bovine serum (FBS), 100 µ/ml penicillin, 100 µ/ml streptomycin, 290 µ/ml glutamine) and cultured (37° C., 5% $CO_2$) overnight. Subsequently, culture media was exchanged with media containing 1% FBS. Solvent control (dimethyl sulfoxide (DMSO); final concentration 1% V/V) or benzodiazepine at concentrations of 2.5–20 µM was added. After 18 hours cell viability was assessed using the MTT assay as previously described in this application. FIG. 11 demonstrates that benzodiazepine kills D2 cells in a dose-response fashion.

To test the effect of benzodiazepine on neuroblastoma tumor growth, $1 \times 10^7$ D2 cells were aseptically inoculated into the thigh musculature of each of eight six-week old nu/nu female mice (Jackson Labs). Beginning one week after tumor cell inoculation, 4 mice were dosed with DMSO (20 µl injected into the peritoneal cavity every day) and 4 mice were dosed with benzodiazepine (2.5 mg dissolved in 20 µl DMSO injected in the peritoneal cavity every day). The mice were evaluated regularly for tumor development and once present the size of the primary tumor was measured every other day. Table 7 demonstrates that in mice that formed tumors, treatment with benzodiazepine significantly decreased the rate of tumor growth.

TABLE 7

| Treatment and control mice with tumors | Days for tumor volume to increase 5 fold |
|---|---|
| Mouse 1 with Compound 1 | 9 |
| Mouse 2 with Compound 1 | 12 |
| Mouse 3 with Compound 1 | 9 |
| Mouse 4 with Compound 1 | 16 |
| Mouse 5 with DMSO 2 | 3 |
| Mouse 6 with DMSO 3 | 5 |

Administration of Benzodiazepine slows rate of neuroblastoma tumor growth in nu/nu mice ($p<0.02$).

Specifically, tumors in control mice increased in volume 5-fold over an average 4 day period, whereas 12 days were required for the same increase in tumor size in benzodiazepine-treated animals ($p<0.02$). These findings support the claim that benzodiazepine is able to treat human malignant disease in a mouse model. Further, benzodiazepine has specific activity against human neuroblastoma both in vitro and in vivo.

Example 6

In another line of experiments we sought to determine if benzodiazepine is able to kill tumor cells that are otherwise resistant to present standard chemotherapy drugs. Ovarian cancer provides an excellent model for studying the problem of chemoresistance in that treatment failures are commonly ascribed to the emergence of chemotherapy resistant cells. The A2780 human ovarian cancer cell line is known to contain wild-type p53; express low levels of bcl-2 and bcl-$x_L$ survival factors; and is sensitive to treatment with cis-platinum(II) diamine dichloride (CDDP), a standard chemotherapeutic for treatment of ovarian cancer. These cells were transfected with an expression vector encoding human bcl-$x_L$, a survival factor that when over-expressed is linked to the development of chemotherapy resistance. These transfected cells are designated 2B 1, and the empty vector transfected controls are designated vector only. A third ovarian cancer cell line, designated SKOV3, was also obtained. This cell line is characterized as: 1. Deficient in wild-type p53 expression; 2. Expressing high levels of endogenous bcl-$x_L$; and 3. Relatively resistant to the cytotoxic actions of CDDP.

Figure 12:
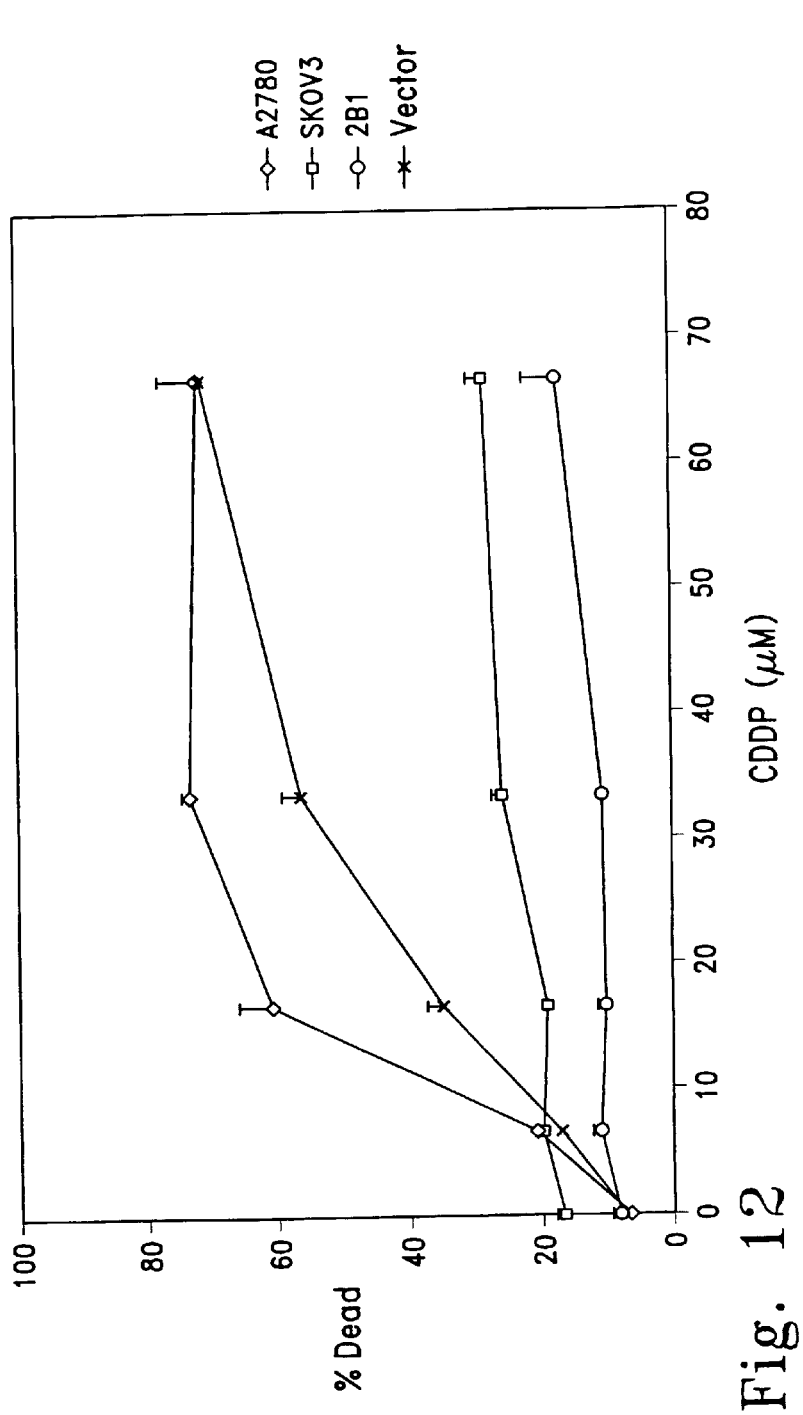
FIG. 12 is a graph that shows that 2B1 and SKOV3 cells are resistant to CDDP.

Each of these cell lines was maintained using standard tissue culture conditions in complete media composed of RPMI, 10% FBS, 100 U/ml penicillin, 100 µ/ml streptomycin, 290 µ/ml glutamine. Each cell type was plated into a series of separate wells on 24-well tissue culture plates at 50,000 cells per well. Approximately 24 hours after plating, media was exchanged to contain the same culture media made with only 2% FBS. At this point either control solvent (DMSO, 1% V/V), increasing concentrations of Compound 1 (4–20 µM), or increasing concentrations of CDDP (6.7–66.7 µM) was added to cells. After twenty-four hours of culture all cells present in each well were removed using trypsin-EDTA and mixed with propidium iodide (final concentration 1 µ/ml). After incubating 20 minutes cells were analyzed by flow cytometry (Coulter FACS Calibur) to determine cell death on the basis of plasma membrane integrity measured as the fraction of cells that had taken-up propidium iodide. FIG. 12 demonstrates that the predicted pattern of chemosensitivity and resistance towards CDDP (A2780 and vector sensitive; 2B 1 and SKOV3 resistant) was observed. FIG. 13 demonstrates that benzodiazepine kills each of these types, irrespective of CDDP resistance. Further, benzodiazepine kills ovarian cancer cells that are resistant to standard chemotherapy. Further, benzodiazepine kills tumor cells that express high levels of survival factors (bcl-$x_L$), as well as those that are deficient in p53 expression.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

We claim:

1. A method of treating psoriasis, comprising administering to a subject an effective amount of a benzodiazepine compound having the structure:

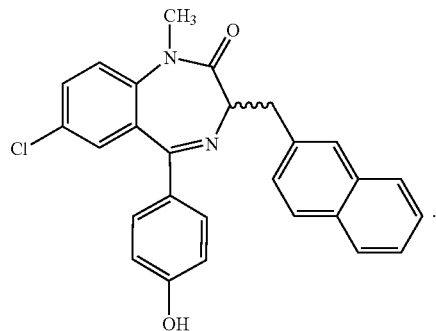

2. The method of claim 1, further comprising co-administering one or more additional agents to the subject.

3. The method of claim 2, wherein the additional agent is a chemotherapeutic agent or radiation.

4. The method of claim 1, wherein the compound is administered orally, parenterally, topically or intranasally.

* * * * *